(12) United States Patent
Xu et al.

(10) Patent No.: US 6,759,255 B2
(45) Date of Patent: Jul. 6, 2004

(54) METHOD AND SYSTEM FOR DETECTING METAL CONTAMINATION ON A SEMICONDUCTOR WAFER

(75) Inventors: Zhiwei Xu, Sunnyvale, CA (US); Arun Srivatsa, Fremont, CA (US); Amin Samsavar, San Jose, CA (US); Thomas G Miller, Sunnyvale, CA (US); Greg Horner, Santa Clara, CA (US); Steven Weinzierl, Hudson, OH (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 126 days.

(21) Appl. No.: 09/854,177

(22) Filed: May 10, 2001

(65) Prior Publication Data

US 2002/0090746 A1 Jul. 11, 2002

Related U.S. Application Data

(60) Provisional application No. 60/203,538, filed on May 10, 2000.

(51) Int. Cl.[7] .............................................. H01I 21/66
(52) U.S. Cl. ........................... 438/14; 438/17; 324/765; 324/769
(58) Field of Search ..................... 438/14, 17; 324/765, 324/769

(56) References Cited

U.S. PATENT DOCUMENTS

| | | |
|---|---|---|
| 3,495,269 A | 2/1970 | Mutschler et al. |
| 3,496,352 A | 2/1970 | Jugle |
| 4,599,558 A | 7/1986 | Castellano, Jr. et al. |
| 4,734,721 A | 3/1988 | Boyer et al. |
| 4,812,756 A | 3/1989 | Curtis et al. |
| 5,485,091 A | 1/1996 | Verkuil |
| 5,594,247 A | 1/1997 | Verkuil et al. |
| 5,644,223 A | 7/1997 | Verkuil |

(List continued on next page.)

FOREIGN PATENT DOCUMENTS

WO          98/57358          12/1998

OTHER PUBLICATIONS

Cosway et al., Manufacturing Implementation of Corona Oxide Silicon (COS) Systems for Diffusion Furnace Contamination Monitoring, 1997 IEEE/SEMI Advanced Semiconductor Manufacturing Conference and Workshop ASMC 97 Proceedings, Cambridge, MA, USA, Sep. 10–12.*

(List continued on next page.)

Primary Examiner—Amir Zarabian
Assistant Examiner—Jeff Vockrodt
(74) Attorney, Agent, or Firm—Ann Marie Mewherter; Conley Rose, P.C.

(57) ABSTRACT

A method to detect metal contamination on a semiconductor topography is provided. The semiconductor topography may include a semiconductor substrate or a dielectric material disposed upon a semiconductor substrate. The metal contamination may be driven into the semiconductor substrate by an annealing process. Alternatively, the annealing process may drive the metal contamination into the dielectric material. Subsequent to the annealing process, a charge may be deposited upon an upper surface of the semiconductor topography. An electrical property of the semiconductor topography may be measured. A characteristic of at least one type of metal contamination may be determined as a function of the electrical property of the semiconductor topography. The method may be used to determine a characteristic of one or more types of metal contamination on a portion of the semiconductor topography or the entire semiconductor topography. A system configured to detect metal contamination on a semiconductor topography is also provided. An oven may be incorporated into the system and may be used to anneal the semiconductor topography. The system may also include a device that may be configured to deposit a charge on an upper surface of the semiconductor topography. A sensor may also be included in the system. The sensor may use a non-contact work function technique to measure an electrical property of the semiconductor topography.

49 Claims, 12 Drawing Sheets

U.S. PATENT DOCUMENTS

| | | |
|---|---|---|
| 5,650,731 A | 7/1997 | Fung et al. |
| 5,661,408 A | 8/1997 | Kamieniecki et al. |
| 5,742,658 A | 4/1998 | Tiffin et al. |
| 5,767,693 A | 6/1998 | Verkuil |
| 5,773,989 A * | 6/1998 | Edelman et al. ............ 324/765 |
| 5,834,941 A | 11/1998 | Verkuil |
| 5,852,232 A | 12/1998 | Samsavar et al. |
| 5,866,806 A | 2/1999 | Samsavar et al. |
| 5,948,972 A | 9/1999 | Samsavar et al. |
| 5,955,661 A | 9/1999 | Samsavar et al. |
| 6,011,404 A * | 1/2000 | Ma et al. ................... 324/765 |
| 6,060,709 A | 5/2000 | Verkuil et al. |
| 6,072,320 A | 6/2000 | Verkuil |
| 6,091,257 A | 7/2000 | Verkuil et al. |
| 6,097,196 A | 8/2000 | Verkuil et al. |
| 6,104,206 A | 8/2000 | Verkuil |
| 6,121,783 A | 9/2000 | Horner et al. |
| 6,191,605 B1 | 2/2001 | Miller et al. |
| 6,201,999 B1 | 3/2001 | Jevtic |
| 6,202,029 B1 | 3/2001 | Verkuil et al. |
| 6,224,638 B1 | 5/2001 | Jevtic et al. |
| 6,267,005 B1 | 7/2001 | Samsavar et al. |
| 6,569,691 B1 * | 5/2003 | Jastrzebski et al. ........... 438/14 |

OTHER PUBLICATIONS

Miller, "A New Approach for Measuring Oxide Thickness," Semiconductor International, Jul. 1995, pp. 147–148.

*Numerical Recipies in C, The Art of Scientific Computing, 2nd Ed.*, © Cambridge University Press 1988, 1992, p. 683.

Weinberg, "Tunneling of Electrons from Si into Thermally Grown $SiO_2$," Solid–State Electronics, 1977, vol. 20, pp. 11–18.

Verkuil, "Rapid Contactless Method for Measuring Fixed Oxide Charge Associated with Silicon Processing," IBM Technical Disclosure Bulletin, vol. 24, No. 6, 1981, pp. 3048–3053.

"Contactless Photovoltage vs. Bias Method for Determining Flat–Band Voltage," IBM Technical Disclosure Bulletin, vol. 32, vol. 9A, 1990, pp. 14–17.

"Contactless Electrical Equivalent Oxide Thickness Measurement," IBM Technical Disclosure Bulletin, vol. 29, No. 10, 1987, pp. 4622–4623.

* cited by examiner

METHOD AND SYSTEM FOR DETECTING METAL CONTAMINATION ON A SEMICONDUCTOR WAFER

PRIORITY CLAIM

This application claims priority to U.S. Provisional Application No. 60/203,538 entitled "Method and System for Detecting Metal Contamination on a Semiconductor Wafer," filed May 10, 2000.

BACKGROUND OF THE INVENTION

1. Field of the Invention

This invention generally relates to detecting metal contamination. Certain embodiments relate to determining metal contamination in a semiconductor substrate or a dielectric material by measuring electrical parameters of the semiconductor substrate or the dielectric material.

2. Description of the Related Art

Metal contamination on a semiconductor substrate may degrade the electrical properties of the semiconductor substrate. For example, metal contamination in the bulk semiconductor substrate may cause the bulk minority carrier lifetime to decrease because the metal contamination may assist in the recombination of electrons and holes in the semiconductor substrate. When metal contamination is present in a dielectric material formed upon the semiconductor substrate or on a surface of the semiconductor substrate, the metal contamination may cause the electrical properties of the dielectric material to degrade. As such, the electrical properties of the dielectric material and the semiconductor substrate may be measured to determine the amount of metal contamination. Metal contamination may have a significant impact on the performance and reliability of semiconductor devices. Metal contamination may be deposited on a semiconductor wafer during processing and manufacturing of semiconductor devices. In many cases, a portion or substantially all of the metal contamination may be deposited on the surface of the semiconductor substrate due to problems in processing or improper handling of the semiconductor substrates.

The metal contamination may currently be measured by physical analysis of a dielectric material or a semiconductor substrate. Examples of physical analysis techniques include, but are not limited to, secondary ion mass spectroscopy (SIMS), total reflection x-ray fluorescence (TXRF), and vapor phase decomposition inductively coupled plasma mass spectroscopy (VPD-ICPMS). The disadvantage to using one of these physical analysis techniques to determine the metal contamination is that these measurement techniques generally take a very long time. As such, the throughput or the number of wafers which may be processed in a given period of time may be relatively low compared to the number of wafers which may need to be examined during a manufacturing process. In addition, SIMS and VPD-ICPMS are destructive techniques which generally require removal of a portion of the dielectric material or semiconductor substrate during the measurement process.

The metal contamination may also currently be measured using device-based electrical characterization. These testing techniques may provide a measurement of the metal contamination that is very similar to metal contamination found on manufactured semiconductor devices. This type of testing, however, requires forming semiconductor devices on the dielectric material or on the semiconductor substrate. As such, device-based electrical characterization may be expensive and time consuming. In addition, analyzing the data also becomes complicated due to the number of processing steps that may be performed in order to form the semiconductor devices on the dielectric material or on the semiconductor substrate.

The metal contamination, however, may also be determined by using a non-contact work function and a surface photo-voltage measurement technique. This testing technique may include biasing the wafer using a corona charge deposited by a corona charge deposition system. The testing technique may also include measuring the surface voltage by using a work function sensor. Additionally, the band bending of the semiconductor substrate may also be measured using a surface photo-voltage sensor. As such, the surface voltage and the band bending of the semiconductor substrate may be functions of the electrical bias, which may be generated by the charge deposited by using a corona charging device. Examples of non-contact corona charging devices are illustrated in U.S. Pat. No. 4,599,558 to Castellano et al., U.S. Pat. No. 5,594,247 to Verkuil et al., and U.S. Pat. No. 5,644,223 to Verkuil, which are incorporated by reference as if fully set forth herein. Examples of work function sensors and surface photo-voltage sensors are illustrated in U.S. Pat. No. 4,812,756 to Curtis et al., U.S. Pat. No. 5,485,091 to Verkuil, U.S. Pat. No. 5,650,731 to Fung, and U.S. Pat. No. 5,767,693 to Verkuil, which are incorporated by reference as if fully set forth herein. Examples of using work function sensors and surface photo-voltage sensors to measure the electrical properties of dielectric materials are illustrated in U.S. Pat. No. 6,202,029 to Verkuil et al. and U.S. Pat. No. 6,191,605 to Miller et al., which are incorporated by reference as if fully set forth herein. Additional examples of systems and devices which may be used to determine the metal contamination in a semiconductor substrate includes "A New Approach for Measuring Oxide Thickness", Miller, Semiconductor International, July 1995, and is incorporated by reference as if fully set forth herein.

Accordingly, it would be advantageous to develop a nondestructive testing method to rapidly and accurately measure the metal contamination on a semiconductor topography without sacrificing product wafers and without forming semiconductor devices on the semiconductor topography.

SUMMARY OF THE INVENTION

In an embodiment, metal contamination in a dielectric material disposed upon a semiconductor substrate may be detected by annealing the semiconductor substrate such that a portion of the metal contamination is driven into the dielectric material. In some embodiments, the annealing process may be effective to drive only one type of metal contamination into the dielectric material. The annealing process, however, may also be effective to drive at least two types of metal contamination into the dielectric material. After the semiconductor substrate is annealed, an electrical property of the dielectric material may be measured. The electrical property may include a surface voltage, a flatband voltage, an interface trap density, a total dielectric charge of the charged dielectric material, or a determined resistivity of the dielectric material. The measured electrical property may be used to determine a characteristic of the metal contaminant. Characteristics may include determining the presence of metal contaminants, the identity of the metal contaminant, and the concentration of the metal contaminants, or all of the above.

In one embodiment, a charge may be deposited on an upper surface of the dielectric material to facilitate measurement of the electrical property. The charge may be deposited using, e.g., a corona charging technique. The deposited charge may be effective to cause a tunneling condition of the dielectric material. After the charge is deposited on the dielectric material, the tunneling voltage of the dielectric material may be measured. The tunneling voltage may be used to determine a tunneling field of the dielectric material. The tunneling voltage and/or the tunneling field may be used to determine the presence of metal contamination in the dielectric material.

The characteristic of the metal contamination in the dielectric material may be determined as a function of the measured electrical property (e.g., tunneling voltage or the tunneling field). Determining the characteristic of the metal contamination in the dielectric material may include determining a characteristic of one type of metal contamination or characteristics of at least two types of metal contamination. Alternatively, the surface voltage may be measured as a function of time. In this manner, a resistivity of the dielectric material may also be determined.

In a further embodiment, a method for detecting metal contamination in a semiconductor substrate is provided. The semiconductor substrate may have a dielectric material formed thereon. The method may include annealing the semiconductor substrate such that the annealing process is effective to drive only one type of metal contamination into the semiconductor substrate. The annealing process may also be effective to drive more than one type of metal contamination into the semiconductor substrate. A charge may be deposited on the semiconductor substrate, and a surface voltage of the semiconductor substrate may be measured by using a non-contact work function measurement technique. In addition, a pulse of light may be directed toward the semiconductor substrate. In this manner, a surface photo-voltage may also be measured. The surface photo-voltage may be measured as a function of time. A bulk minority carrier lifetime may be determined by using the measured surface photo-voltage of the semiconductor substrate. The surface photo-voltage may also be used to determine a characteristic of the metal contamination in the semiconductor substrate. The characteristic of the metal contamination in the semiconductor substrate may be a function of the measured surface photo-voltage or of the determined bulk minority carrier lifetime. The characteristic may be determined for only one, or more than one type of metal contamination.

In an additional embodiment, a system may be configured to measure a characteristic of metal contamination in a semiconductor topography. The semiconductor topography may include a semiconductor substrate or a dielectric material formed upon an upper surface of a semiconductor substrate. The system may include an oven that may be used to anneal the semiconductor topography. The oven may be configured to heat the semiconductor topography such that only one type of metal contamination may be driven into the semiconductor topography. The oven may also be configured to heat the semiconductor topography such that more than one type of metal contamination may be driven into the semiconductor topography. The system may also include a device that may be used to deposit a charge on an upper surface of the semiconductor topography. The device may include a non-contact corona charging device. The device may be configured to deposit a charge on predetermined regions of the semiconductor topography or on randomly determined regions of the semiconductor topography. The device may also be configured to deposit a charge on a portion of the semiconductor topography or on substantially the entire semiconductor topography. The system may further include a sensor that may be used to measure at least one electrical property of the charged upper surface of the semiconductor topography. The electrical property may include a tunneling voltage or a tunneling field, a surface voltage, a flatband voltage, an interface trap density, or a total dielectric charge of the charged dielectric material. The sensor may include a non-contact work function sensor and a surface photo-voltage measurement device. Furthermore, the system may also include an illumination system, which may be used to direct a pulse of light toward the semiconductor substrate. As such, the illumination system may be used to direct the light toward the semiconductor substrate subsequent to depositing the charge. The sensor may be used to determine a surface photo-voltage of the semiconductor topography. The system may also include an operating system that may be used to determine a characteristic of the metal contamination in the semiconductor substrate. The characteristic may be determined as a function of any of the measured electrical properties described above.

In an embodiment, a method for fabricating a semiconductor device on a semiconductor substrate may also be provided. The semiconductor topography may include a semiconductor substrate or a dielectric material disposed upon the semiconductor substrate. The method may include annealing the semiconductor topography which may be effective to drive at least one type of metal contamination into the semiconductor substrate or the dielectric material. An electrical property of the semiconductor substrate or the dielectric material may be measured. Measuring the electrical property may include depositing a charge on an upper surface of the dielectric material or the semiconductor substrate. The electrical property may be measured using a non-contact work function technique or a non-contact surface photo-voltage measurement technique. The method may further include determining a characteristic of the metal contamination in the semiconductor topography. The characteristic of the semiconductor topography may be a function of the measured electrical property of the dielectric material or the semiconductor substrate. The method may also include comparing the determined characteristic of the metal contamination to a range of acceptable characteristics of the metal contamination. The range of acceptable characteristics of the metal contamination may include levels of the metal contamination that may not substantially hinder the performance of a semiconductor device. As such, if the determined characteristic is within the range of acceptable characteristics of the metal contamination, the method may include forming a semiconductor device on the semiconductor topography.

BRIEF DESCRIPTION OF THE DRAWINGS

Other objects and advantages of the invention will become apparent upon reading the following detailed description and upon reference to the accompanying drawings in which.

Figure 1:
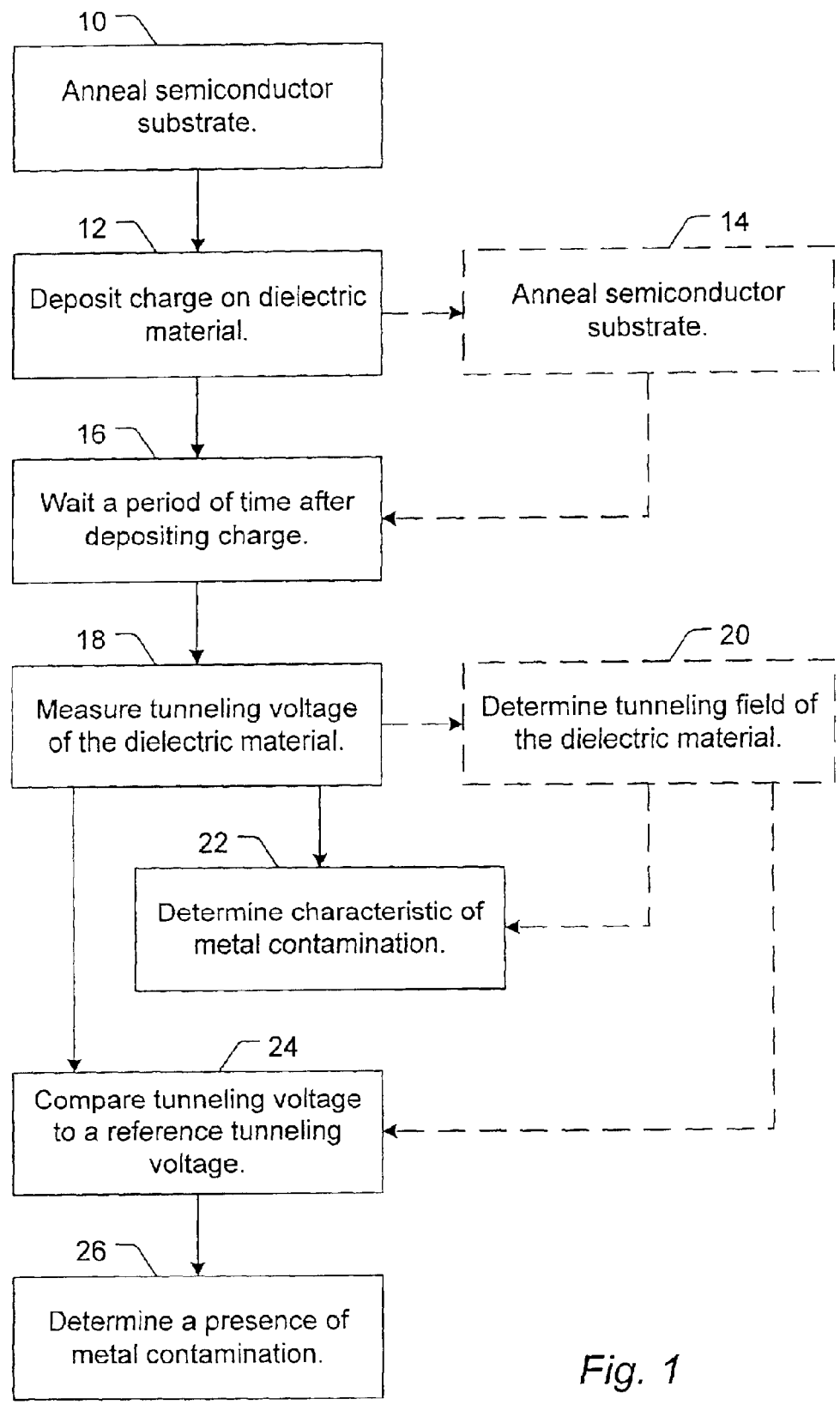
FIG. 1 depicts a flow chart illustrating a method to detect metal contamination in a dielectric material disposed upon a semiconductor substrate that includes measuring a tunneling voltage of the dielectric material.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

Turning now to the drawings, FIG. 1 illustrates an embodiment of a method for detecting metal contamination in a dielectric material disposed upon a semiconductor substrate. Metal contamination that may be detected using this method may include copper, iron, chromium, cobalt, and aluminum. The method may include annealing the semiconductor substrate as shown in step 10. As shown in step 18, the method may also include measuring a tunneling voltage of the dielectric material. In addition, the method may include determining a characteristic of the metal contamination in the dielectric material as shown in step 24. Characteristics may include determining the presence of metal contaminants, the identity of the metal contaminant, the concentration of the metal contaminants, or all of the above. A characteristic of the metal contamination may be a function of the measured tunneling voltage. The characteristic of the metal contamination may also be a function of a temperature at which the semiconductor substrate may be annealed. Additionally, the metal contamination may include only one type of metal contamination or may include more than one type of metal contamination. Furthermore, the metal contamination may include metal contamination in a portion of the dielectric material. For example, the portion of the dielectric material may include a locally contaminated region of the dielectric material.

The semiconductor substrate may be silicon, and is doped either n-type (for producing a p-channel transistor) or p-type (for an n-channel transistor). More specifically, the substrate may be an epitaxial silicon layer grown on a monocrystalline silicon substrate, or an n-type or p-type well region formed in a monocrystalline silicon substrate. Appropriate semiconductor substrates may also include silicon germanium and gallium arsenide. The dielectric material may be silicon dioxide deposited by CVD. In particular, decomposition of tetraethyl orthosilicate (TEOS) may be performed in a plasma-enhanced CVD (PECVD) reactor at a substrate temperature in the range from about 200° C. to about 500° C. to produce a very conformal dielectric film. Other techniques that may be used to form a silicon dioxide dielectric material include PECVD using a silane source, and atmospheric-pressure CVD (APCVD) and low-pressure CVD (LPCVD) using silane or TEOS sources. Additional dielectric materials may also include, but are not limited to, silicon nitride, silicon oxynitride, and various high-k and low-k materials, where k is the dielectric constant of the material. Typically, k is less than about 3.8 for low-k materials and greater than about 4.5 for high-k materials.

Annealing the semiconductor substrate as shown in step 10 may be effective to drive the metal contamination into the dielectric material. The metal contamination may be disposed on an upper surface of the dielectric material prior to the annealing process. In some embodiments, more than one metal contaminant may be disposed upon the upper surface of the dielectric material. The semiconductor substrate may be heated to a temperature during the annealing process such that only one type of metal contamination is driven into the dielectric material. The other metal contaminants will substantially remain on the upper surface. Alternatively, during the annealing process the semiconductor substrate may be heated to a temperature to drive more than one type of metal contamination into the dielectric material.

The annealing process may be performed under ambient conditions or other conditions, such as a $N_2$ rich environment. As such the annealing process may cause degradation of the dielectric material. The annealing process may be performed, however, such that the annealed dielectric material is substantially free of damage. In this manner, the extent to which the metal contamination may be driven into the dielectric material by the annealing process may be limited by an acceptable amount of degradation in the dielectric material which may be caused by the annealing process.

During the annealing process, the semiconductor substrate may be heated to a temperature of less than approximately 1100° C. The temperature of the annealing process may also depend on the type of metal contamination that is being detected. For example, the semiconductor substrate may be heated to a temperature of approximately 350° C. to approximately 500° C. if the metal contamination being driven into the semiconductor substrate includes copper.

The period of time for which the semiconductor substrate may be annealed, however, may also depend on the metal contamination, which is being driven into the dielectric material. In one example, if the metal contamination includes copper, then the semiconductor substrate may be heated for approximately one minute to approximately thirty minutes during an annealing process. In most embodiments, the semiconductor substrate may be annealed for less than approximately one hour.

In an embodiment, a charge may be deposited on an upper surface of the dielectric material. The deposited charge drives the dielectric material to approximately a tunneling condition of the dielectric material as shown in step 12. For positive tunneling field, the deposited charge may be approximately $1 \times 10^{-6}$ $C/cm^2$ to approximately $1 \times 10^{-4}$ $C/cm^2$, and may be equal to approximately $8 \times 10^{-6}$ $C/cm^2$ for a wafer with a low level of surface charge. For negative tunneling field, the deposited charge may be approximately $-1 \times 10^{-6}$ $C/cm^2$ to approximately $-1 \times 10^{-4}$ $C/cm^2$, and may be equal to approximately $-8 \times 10^{-6}$ $C/cm^2$ for a wafer with a low level of surface charge. In one embodiment, the charge may be deposited by using a non-contact corona charging technique. A non-contact corona charging device may include any type of device that may deposit a charge on the surface of the semiconductor substrate. The corona charging device may also be used to deposit a charge on specific portions of the semiconductor substrate. For example, the charge may be deposited on predetermined regions of the upper surface of the dielectric material or on randomly determined regions of the upper surface of the dielectric material. The charge may also be deposited on a portion of the upper surface of the dielectric material or on substantially the entire upper surface of the dielectric material.

As shown in step 16, the method may include waiting a period of time between depositing a charge on an upper surface of the dielectric material and measuring the tunneling voltage of the dielectric material. Small amounts of metal contamination may only shift the leakage current of the dielectric material in the low leakage current portion. Therefore, the waiting time may be optimized to increase the sensitivity of measuring small amounts of metal contamination. The waiting time may be larger or smaller depending on the metal contamination that is being measured. For example, if the metal contamination includes copper, then the period of time may include a waiting time of approximately zero minutes to approximately thirty minutes.

As shown in step 18, a tunneling voltage of the dielectric material may be measured by using a non-contact work function measurement technique. The tunneling voltage may be used to determine a characteristic of the metal contamination in the dielectric material as shown in step 22. The tunneling voltage may also be used to determine a tunneling field of the dielectric material as shown in step 20. A tunneling field may be the electric field strength in the dielectric material at which a deposition rate of the charge may be balanced by charge leakage through the dielectric material. As such, the tunneling field may be the maximum electric field which may be sustained by the corona charging source. The tunneling field may depend on several parameters of the instruments, which may be used to measure the tunneling voltage. For example, a tunneling field of a dielectric material may be affected by characteristics of the corona charging device such as an amount or uniformity of the deposited charge. For a set of instrument parameters, the tunneling field may be used as a measure of the quality of the dielectric material. The tunneling field may also be affected by the period of time between depositing a charge on an upper surface of the dielectric material. Therefore, the sensitivity of the tunneling field of the dielectric material may be increased by optimizing the parameters of the instruments, which may be used to measure the tunneling voltage. The tunneling field may also be used to determine a characteristic of the metal contamination in the dielectric material as shown in step 22. As such, the characteristic may also be a function of parameters of instruments which may be used to measure the tunneling voltage and which may have an effect on the measured tunneling voltage including an amount of the deposited charge.

After measuring a tunneling voltage of the dielectric material, the method may be repeated to determine a characteristic of a different type of metal contamination. For example, the semiconductor substrate may be annealed a second time using a different annealing process subsequent to measuring the tunneling voltage. As such, a second type of metal contamination may be driven into the dielectric material in the second annealing process. A charge may be deposited upon the dielectric material and a tunneling voltage of the dielectric material may be measured. A characteristic of the second type of metal contamination may be determined from the tunneling voltage. In this manner, a characteristic of each type of metal contamination in the dielectric material may be individually determined.

In an embodiment, the tunneling voltage of the dielectric material may also be compared to a tunneling voltage of a reference dielectric material as shown in step 24. Alternatively, a tunneling field of the dielectric material may be compared to a tunneling field of a reference dielectric material in step 24. The reference dielectric material may have substantially the same thickness and substantially the same composition, or quality, as the dielectric material which is being measured. The reference dielectric material may also be substantially free of metal contamination. Alternatively, the reference dielectric material may have a predetermined level of one or more types of metal contamination. The metal contamination in the reference dielectric material may also be predetermined or known. In this manner, comparison of a tunneling voltage of the dielectric material to a tunneling voltage of a reference dielectric material may be used to determine if at least one type of metal contamination is present in the dielectric material as shown in step 26. Comparing the tunneling field of the dielectric material to a tunneling field of a reference dielectric material may also be used to determine if at least one type of metal contamination is present in the dielectric material.

In an embodiment, a tunneling field of a reference dielectric material may also be used to alter a baseline of the tunneling field of the dielectric material. Leakage in the dielectric material may cause the baseline of the tunneling field to drift. In addition, variations in a period of time that may elapse between depositing the charge and measuring the tunneling voltage at different positions on the dielectric material may also cause the baseline of the tunneling field to drift. For example, the tunneling field of a reference dielectric material may be subtracted from a tunneling field of the dielectric material. The reference dielectric material may have a similar thickness and original, or pre-processing, quality as the dielectric material being measured. In addition, the reference dielectric material may be substantially free of metal contamination. The leakage of the dielectric material may also be determined by measuring a charge decay at a predetermined position on the dielectric material. In this manner, correcting the baseline may include using the measured leakage to determine the tunneling field of the dielectric material.

In an additional embodiment, the tunneling voltage may be measured at various positions on the dielectric material in order to determine the metal contamination in a region of the semiconductor substrate. Variations in the time that may elapse between depositing the charge and measuring the tunneling voltage at the various positions may also be minimized in order to alter a baseline of the tunneling field data. In an embodiment, a charge may be deposited on a portion of the dielectric material subsequent to annealing the semiconductor substrate. The tunneling voltage for this portion of the dielectric material may be measured. This procedure may be repeated for additional portions of the dielectric material such that a tunneling voltage for substantially the entire dielectric material may be measured. As such, the time that may elapse between depositing the charge and measuring a tunneling voltage at the various positions may be minimized. Furthermore, the semiconductor substrate may be moved under the corona charging device and under the work function sensor by using a movable chuck. As such, variations in the time that may elapse between depositing the charge and measuring a tunneling voltage may be minimized by matching the time required to deposit the charge and the time required to measure the tunneling voltage.

In an embodiment, an electrical property of the dielectric material such as a tunneling voltage may be measured at more than one position on the semiconductor substrate. As such, an additional electrical property such as a tunneling field of the dielectric material may also be determined at each measurement position on the semiconductor substrate. Furthermore, a characteristic of at least one type of metal contamination may also be determined at each measurement position. In this manner, a plot of the measured electrical property data, the determined electrical property data, or the determined characteristic of the metal contamination in the dielectric material as a function of measurement position may be generated. A plot of the data as a function of the measurement position may be used to determine variations in the data across the dielectric material. Therefore, variations in the plotted data may indicate a presence of metal contamination in locally contaminated regions of the dielectric material.

In an embodiment, the generated plot of the data as a function of measurement position may also be compared to a predetermined plot of data for a reference dielectric material. The predetermined plot of data may include predetermined electrical property data or predetermined characteristic data of the metal contamination in the dielectric material as a function of measurement position. The reference dielectric material may be substantially free of metal contamination. As such, comparing the plot of the measured data to a plot of predetermined data may indicate a presence or an extent of the metal contamination in a dielectric material. In a further embodiment, the predetermined plot of data as a function of measurement position may be representative of a range of acceptable levels of at least one type of metal contamination. Acceptable levels of the metal contamination may include levels of metal contamination that may not substantially hinder the performance of a semiconductor device formed on the semiconductor substrate. Therefore, comparing the generated plot of data for the dielectric material to the range of acceptable levels of metal contamination may indicate if a semiconductor substrate may be used in subsequent processing to form a semiconductor device thereon. The acceptable levels of metal contamination may also be used to monitor the performance or the presence of contamination in a processing device, which may have been used to process the semiconductor topography prior to determining the characteristic of the metal contamination.

In an embodiment, the method may also include annealing the semiconductor substrate subsequent to depositing the charge on the upper surface of the semiconductor substrate as shown in step 14. Annealing the semiconductor substrate subsequent to depositing the charge may include heating the semiconductor substrate to an annealing temperature of less than approximately 120° C. As such, annealing the semiconductor substrate subsequent to depositing the charge may cause charge leakage from the dielectric material. In this manner, the defects in the dielectric material due to the metal contamination may be enhanced. In particular, this method may be used to enhance defects caused by copper metal contamination in a dielectric material such as silicon dioxide.

In an additional embodiment, the method may also include generating multiple extended electrical stress cycles in the dielectric material prior to measuring a tunneling voltage of the dielectric material. Electrical stress in the dielectric material may be generated by depositing a charge on an upper surface of the dielectric material. The charge may be deposited by using a non-contact corona charging technique. The generated electrical stress may include an electrical stress of approximately $-1\times10^{-3}$ C/cm$^2$ to approximately $+1\times10^{-3}$ C/cm$^2$, and may include an electrical stress from approximately $3\times10^{-5}$ C/cm$^2$ to approximately $1\times10^{-3}$ C/cm$^2$ for positive stress and from approximately $-3\times10^{-5}$ C/cm$^2$ to $-1\times10^{-3}$ C/cm$^2$ for negative stress. Thie dielectric material may degrade under extended electrical stress. In addition, the degradation rate as a function of electrical stress may also be a function of the defect density in the dielectric material, which may be caused by metal contamination in the dielectric material prior to the electrical stress cycles. Therefore, very low levels of metal contamination may be detected by repeatedly generating electrical stress in the dielectric material to increase degradation of the dielectric material caused by the metal contamination. In addition, the parity of the stress cycles may also be changed to cause further degradation of the dielectric material. Subsequent to generating each electrical stress in the dielectric material, the semiconductor substrate may be heated to a temperature of approximately 50° C. to approximately 120° C. The semiconductor substrate may be heated for a period of time of approximately one minute to approximately thirty minutes. Heating the semiconductor substrate subsequent to each electrical stress cycle may further increase the degradation of the dielectric material caused by metal contamination, which may further enhance the capability to detect very low levels of metal contamination.

In an additional embodiment, the method may also be used to detect particulate contamination on an upper surface of the dielectric material. Particulate contamination may include non-metallic sub-micron particles that may be deposited on the dielectric material during handling and processing. By increasing the mobility of the deposited charge, the charge may be deposited through the dielectric material underlying the particulate contamination. The mobility of the deposited charge may be increased by flowing a gas across the upper surface of the dielectric material. The gas may include a gas that may have a moisture content which is greater than a moisture content of the ambient air surrounding the semiconductor substrate being measured. In addition, the gas may include ammonia. As such, a characteristic of the particulate contamination in the dielectric material may be determined as a function of the measured tunneling voltage.

Figure 2:
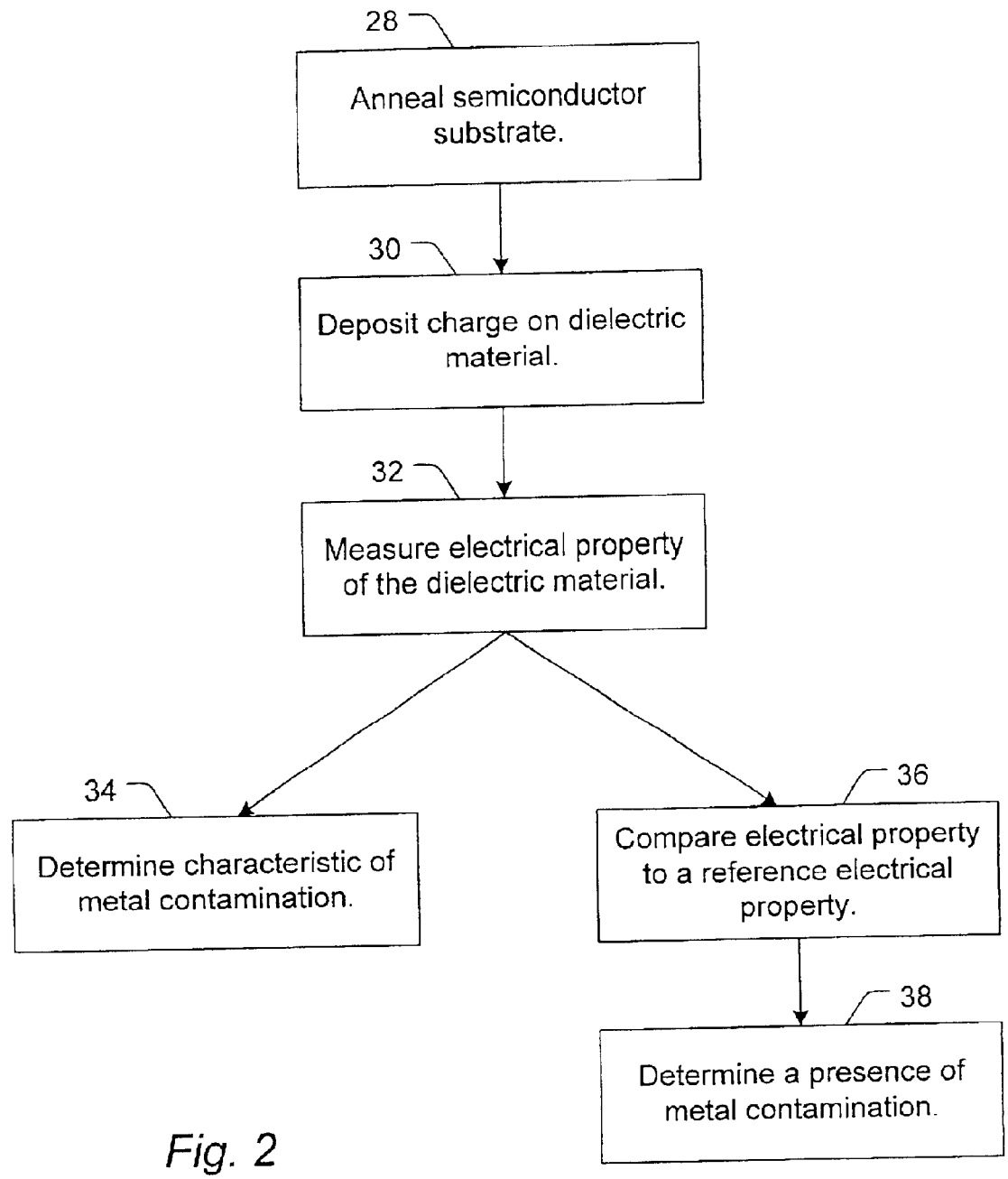
FIG. 2 depicts a flow chart illustrating a method to detect metal contamination in a dielectric material disposed upon a semiconductor substrate that includes measuring an electrical property of the dielectric material.

FIG. 2 illustrates an additional embodiment of a method to detect metal contamination in a dielectric material disposed upon a semiconductor substrate. As shown in step 28, the semiconductor substrate may be annealed. The annealing process may be effective to drive the metal contamination into the dielectric material. The annealing process may also be performed as described in an above embodiment. A charge may be deposited upon an upper surface of the dielectric material as shown in step 30. The charge may be deposited as described in an above embodiment. As shown in step 32, an electrical property of the dielectric material may be measured. The electrical property may also be measured as described in an above embodiment. The electrical property of the dielectric material may include a surface voltage $V_S$, flatband voltage $V_{fb}$, an interface trap density $D_{it}$, or a total dielectric charge of the dielectric material. Furthermore, the method may include determining a characteristic of the metal contamination in the dielectric material as shown in step 34. The characteristic of the metal contamination may be a function of the measured electrical property of the dielectric material. In addition, the characteristic may be determined using any of the techniques, which are described in an above embodiment. For example, as shown in step 36, the electrical property may be compared to an electrical property of a reference dielectric material. The reference dielectric material may be substantially free of metal contamination. Alternatively, the reference dielectric material may have a predetermined characteristic of a known type of metal contamination. In this manner, as shown in step 38, comparing the measured electrical property of the dielectric material to an electrical property of a reference dielectric material may be used to indicate a presence of the metal contamination in the measured dielectric material.

A flatband voltage may be representative of the metal contamination in the dielectric material and at an interface between the dielectric material and the semiconductor substrate. An interface trap density may be representative of the metal contamination at the interface between the dielectric material and the semiconductor substrate. When measuring the flatband voltage or the interface trap density, a deposited charge on an upper surface of the dielectric material may be sufficient to drive the semiconductor substrate to accumulation. Subsequent to measuring a surface potential of the dielectric material, a small amount of charge may be deposited upon the upper surface of the dielectric material by a second charge deposition step. A polarity of the charge which may be deposited during the second charge deposition step may be opposite of the polarity of the charge deposited prior to measuring the surface potential. In this manner, the semiconductor substrate may be driven toward inversion. The steps of alternately driving the semiconductor substrate to accumulation and toward inversion may be repeated until the semiconductor substrate reaches inversion. The measurements of the surface voltage after each step of driving the semiconductor substrate to accumulation and toward inversion may be used to generate a Q-V sweep. The flatband voltage and the interface trap density may be determined from the generated Q-V sweep.

In an additional embodiment, the measured electrical property of the dielectric material may be used to determine a resistivity of the dielectric material. A resistivity of the dielectric material may be closely related to the bias applied to the dielectric material. Therefore, the resistivity of the dielectric material may depend on the voltage being generated by the deposited charge and the metal contamination in the dielectric material. As such, an optimized sensitivity in the measurement of the resistivity of the dielectric material may be biased to approximately a tunneling field of the dielectric material by using the corona charging technique.

For example, the deposited charge may be effective to generate an electrical field of the dielectric material of approximately 1 MV/cm to approximately 9 MV/cm for positive bias, and approximately −1 MV/cm to approximately −9 MV/cm for negative bias. The measured electrical property that may be measured may include a surface voltage of the dielectric material, which may be measured as a function of time. The measured electrical property may be used to determine a resistivity of the dielectric material. The resistivity of the dielectric material may be determined by using the following equation:

$$\rho_{dielectric} = -V/[(dV/dt) \cdot \epsilon \cdot \epsilon_0],$$

where $\rho_{dielectric}$ is the resistivity of the dielectric material, V is the measured surface voltage of the dielectric material, t is the decay time, $\epsilon$ is the dielectric constant of the dielectric material, and $\epsilon_0$ is the vacuum permittivity. The determined characteristic of the metal contamination in the dielectric material may, therefore, also be a function of the resistivity of the dielectric material.

Figure 3:
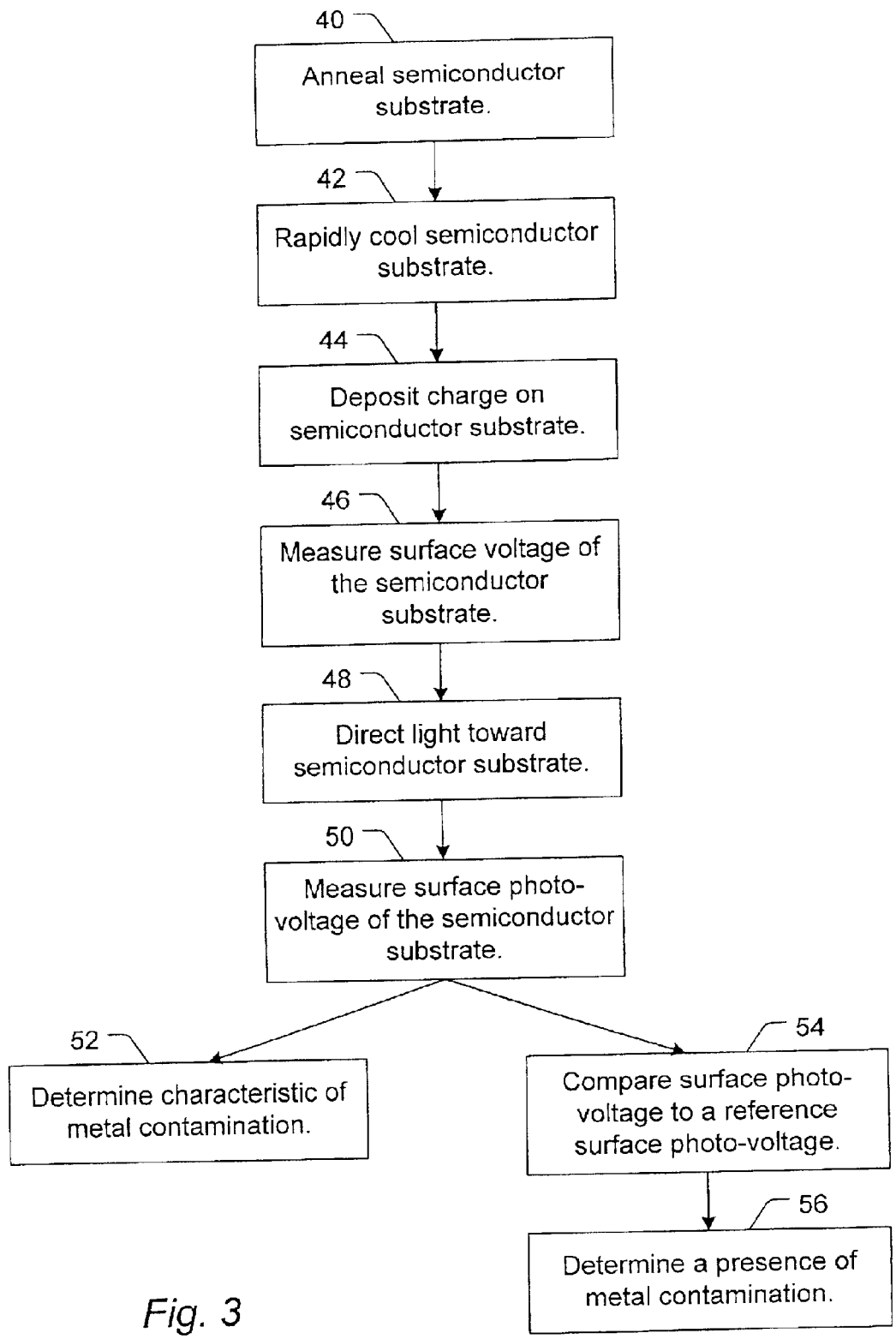
FIG. 3 depicts a flow chart illustrating a method to detect metal contamination in a semiconductor substrate.

FIG. 3 illustrates an embodiment of a method for detecting metal contamination in a semiconductor substrate. The metal contamination that may be detected by using the method may include, but is not limited to, copper, aluminum, chromium, cobalt, and iron. The semiconductor substrate may include material which is described in an above embodiment including monocrystalline silicon, silicon germanium, and gallium arsenide. The semiconductor substrate may have a dielectric material formed on an upper surface of the semiconductor substrate. The dielectric material may be formed on the semiconductor substrate prior to annealing the semiconductor substrate.

As shown in step 40, the semiconductor substrate may be annealed by heating the semiconductor substrate to an annealing temperature of less than approximately 1100° C. The annealing process may be effective to drive the metal contamination into the semiconductor substrate. The annealing process may be effective to drive only one type of metal contamination into the semiconductor substrate. Alternatively, the annealing process may be effective to drive at least two types of metal contamination into the semiconductor substrate. As such, the annealing temperature of the annealing process may depend on the type of metal contamination that may be driven into the semiconductor substrate. For example, for copper metal contamination, an annealing temperature of approximately 350° C. to approximately 500° C. may be used to anneal the semiconductor substrate. The annealing process may also include heating the semiconductor substrate for a period of time. The period of time may also depend on the type of metal contamination that may be driven into the semiconductor substrate. For copper metal contamination, a period of time of approximately one minute to approximately thirty minutes, or a period of time of approximately less than ten minutes may be used to anneal the semiconductor substrate.

As shown in step 42, the method may also include rapidly cooling the semiconductor substrate following the annealing process. The semiconductor substrate may be cooled such that the metal contamination may be prevented from diffusing out of the semiconductor substrate. Rapidly cooling the semiconductor substrate may include removing the semiconductor substrate from a device that may be used to anneal the semiconductor substrate. A chill plate which may be maintained at a temperature that may be significantly lower than the temperature to which the semiconductor substrate may be heated during the annealing process may be used to cool the semiconductor substrate. Cooling the semiconductor substrate may also include cooling a semiconductor substrate using any natural or forced convection cooling methods known in the art.

The method may also include depositing a charge on an upper surface of the semiconductor substrate or on an upper surface of a dielectric material disposed upon the semiconductor substrate as shown in step 44. A charge may be deposited upon an upper surface by using a non-contact corona charging technique. The deposited charge may be approximately $-1 \times 10^{-4}$ C/cm$^2$ to approximately $1 \times 10^{-4}$ C/cm$^2$. The deposited charge may be effective to drive the semiconductor substrate to depletion. As described in an above embodiment, the charge may be deposited upon various regions of the upper surface of the semiconductor substrate or the dielectric material disposed upon the semiconductor substrate. Regions of the semiconductor substrate may include predetermined or randomly determined regions of the semiconductor substrate or substantially the entire semiconductor substrate. As shown in optional step 46, subsequent to depositing the charge, a surface voltage of the semiconductor substrate may be measured by using a non-contact work function technique.

A pulse of light may be directed toward the semiconductor substrate as shown in step 48. The intensity of the pulse of light may be predetermined to generate a surface photo-voltage of the semiconductor substrate that may be within approximately 90% of the saturation value of the surface photo-voltage. As shown in step 50, a surface photo-voltage of the semiconductor substrate may be measured. The surface photo-voltage may be measured by using a non-contact work function technique or a surface photo-voltage measurement technique. The surface photo-voltage may be representative of the band bending of the semiconductor substrate, which may result from metal contamination in the semiconductor substrate. The band bending of the semiconductor substrate may be a function of the electrical bias of the semiconductor substrate, which may result from the deposited charge. The surface photo-voltage may also be measured as a function of delay time. Subsequent to measuring the surface photo-voltage of the semiconductor substrate, the method may be repeated using the same semiconductor substrate. The second method may be carried out by using a different annealing process such that a different type of metal contamination may be driven into the semiconductor substrate In this manner, each type of metal contamination that may be present in the semiconductor substrate may be individually measured.

The surface photo-voltage may also be used to determine a bulk minority carrier lifetime, $\tau_{BR}$, of the semiconductor substrate. The bulk minority carrier lifetime may be representative of the metal contamination in the semiconductor substrate. A semiconductor substrate which may be substantially free of metal contamination may have a bulk minority carrier lifetime of approximately 0.5 ms or longer. Metal contamination in a semiconductor substrate may effectively promote recombination of electrons and holes that are produced during the method. Therefore, metal contamination that may be present in the semiconductor substrate may reduce the bulk minority carrier lifetime.

As shown in step 52, a characteristic of the metal contamination in the semiconductor substrate may be determined as a function of a measured surface voltage, a measured surface photo-voltage, or a determined bulk minority carrier lifetime. The characteristic of the metal contamination in the semiconductor substrate may also be a function of the annealing temperature or the corona field strength. In addition, the characteristic of the metal contamination in the semiconductor substrate may be a function of only one type of metal contamination or of at least two types of metal contamination. The characteristic of the metal contamination may also be determined for a portion of the semiconductor substrate, which may have a charge, deposited thereon. As such, the characteristic of the metal contamination may be used to determine locally contaminated regions of the semiconductor substrate.

As shown in step 54, the measured surface photo-voltage may be compared to a surface photo-voltage of a reference semiconductor substrate. The reference semiconductor substrate may be substantially free of metal contamination. Alternatively, the reference semiconductor substrate may include a predetermined level of at least one type of known, or predetermined, metal contamination. Comparing the measured surface photo-voltage to a reference surface photo-voltage may be used to determine a presence of metal contamination in the semiconductor substrate as shown in step 56.

In an embodiment, an electrical property of the semiconductor substrate such as a surface photo-voltage may be measured at more than one position on the semiconductor substrate. As such, an additional electrical property such as a bulk minority carrier lifetime of the semiconductor substrate may also be determined at each measurement position. Furthermore, a characteristic of at least one type of metal contamination may also be determined at each measurement position. In this manner, a plot of the measured electrical property data, the determined electrical property data, or the determined characteristic of the metal contamination in the semiconductor substrate as a function of measurement position may be generated. A plot of the data as a function of the measurement position may be used to determine variations in the data across the semiconductor substrate. Therefore, variations in the plotted data may indicate a presence of metal contamination in locally contaminated regions of the semiconductor substrate.

In an embodiment, the generated plot of the data as a function of measurement position may also be compared to a predetermined plot of data for a reference semiconductor substrate. The predetermined plot of data may include predetermined electrical property data or predetermined characteristic data of the metal contamination in the semiconductor substrate as a function of measurement position. The reference semiconductor substrate may be substantially free of metal contamination. As such, comparing the plot of the measured data to a plot of predetermined data may indicate a presence or an extent of the metal contamination in a semiconductor substrate. In a further embodiment, the predetermined plot of data as a function of measurement position may be representative of a range of acceptable levels of at least one type of metal contamination. Acceptable levels of the metal contamination may include levels of metal contamination that may not substantially hinder the performance of a semiconductor device formed on the semiconductor substrate. Therefore, comparing the generated plot of data for the measured semiconductor substrate to a range of acceptable levels of metal contamination may indicate if the semiconductor substrate may be used in subsequent processing to form a semiconductor device thereon. The acceptable levels of metal contamination may also be used to monitor the performance or the presence of contamination in a processing device that may have been used to process the semiconductor topography prior to determining the characteristic of the metal contamination.

A set of data may be collected and analyzed which may include electrical properties such as tunneling voltages associated with a characteristic of metal contamination on a semiconductor topography. The semiconductor topography may include a semiconductor substrate or a dielectric material disposed upon a semiconductor substrate. In an embodiment, a measured electrical property such as a tunneling voltage of a semiconductor topography may be compared to a set of such data In this manner, a characteristic of the metal contamination in the semiconductor topography may be determined. The set of data may be generated by using one device to measure an electrical property and to determine a characteristic of the metal contamination as a function of the electrical property. Alternatively the set of data may be generated by several devices that may be similarly configured to measure an electrical property and to determine a characteristic of the metal contamination as a function of the electrical property. The set of data may be used to calibrate or to check the accuracy of additional similarly configured devices. In a manufacturing environment, several similarly configured devices may be used to simultaneously manufacture multiple lots of semiconductor devices. Therefore, using the set of data to calibrate and check multiple tools may be particularly important in semiconductor manufacturing to ensure that the level of metal contamination on each semiconductor topography on which devices are being fabricated may be accurately determined.

In addition, a semiconductor topography may be intentionally contaminated with an amount of metal. An electrical property such as a tunneling voltage may be measured for the contaminated semiconductor topography. Additional semiconductor topographies may also be contaminated with varying amounts of metal. Electrical properties of the additional contaminated semiconductor topographies may also be measured. A characteristic of the metal contamination may be determined for each electrical property associated with a contaminated semiconductor topography. In this manner, a quantitative relationship may be determined between a characteristic of the metal contamination on a semiconductor topography and variations in a measured electrical property of the semiconductor topography. Furthermore, a determined quantitative relationship which describes a relationship between the characteristic of the metal contamination and the associated electrical properties may be used to determine the amount of metal contamination in an unknown, or product, semiconductor topography. The determined quantitative relationships may be used during processing of semiconductor devices to determine if a level of the metal contamination on a semiconductor topography is low enough such that the semiconductor topography may be used to successfully manufacture semiconductor devices.

Furthermore, this algorithm may be integrated into a controller for a system that may be configured to measure the metal contamination in a semiconductor topography. Alternatively, an algorithm which describes a theoretical, or mathematical, relationship between an electrical property of a semiconductor topography and a characteristic of the metal contamination in the semiconductor topography may be integrated into a controller for the system. In an embodiment, the system may include an oven that may be used to anneal the semiconductor substrate, a device that may be used to deposit a charge on an upper surface of the semiconductor topography, and a sensor that may be used to measure an electrical property of the semiconductor topography. The semiconductor topography may include a semiconductor substrate or a dielectric material deposited upon a semiconductor substrate. The controller may be a computer system configured to operate software and control the system to anneal the semiconductor topography, to deposit a charge on an upper surface of the dielectric material, and to measure an electrical property of the semiconductor topography. In an additional embodiment, the system may also include a robotic wafer handler, a pre-aligner, a cooling device, a movable chuck, and an illumination system. Therefore, the controller may be further configured to control the robotic wafer handler, the pre-aligner, the cooling device, the movable chuck, and the illumination system.

The computer system may include a memory medium on which computer programs for operating the device and performing calculations related to the data collected. The term "memory medium" is intended to include an installation medium, e.g., a CD-ROM, or floppy disks, a computer system memory such as DRAM, SRAM, EDO RAM, Rambus RAM, etc., or a non-volatile memory such as a magnetic media, e.g., a hard drive, or optical storage. The memory medium may comprise other types of memory as well, or combinations thereof. In addition, the memory medium may be located in a first computer in which the programs are executed, or may be located in a second, or different, computer that connects to the first computer over a network. In the latter instance, the second computer provides the program instructions to the first computer for execution. Also, the computer system may take various forms, including a personal computer system, mainframe computer system, workstation, network appliance, Internet appliance, personal digital assistant (PDA), television system or other device. In general, the term "computer system" may be broadly defined to encompass any device having a processor which executes instructions from a memory medium.

The memory medium may store a software program for the operation of the optical inspection device. The software program may be implemented in any of various ways, including procedure-based techniques, component-based techniques, and/or object-oriented techniques, among others. For example, the software program may be implemented using ActiveX controls, C++ objects, JavaBeans, Microsoft Foundation Classes (MFC), or other technologies or methodologies, as desired. A CPU, such as the host CPU, executing code and data from the memory medium may include creating and executing the software program according to the methods described above.

Various embodiments further include receiving or storing instructions and/or data implemented in accordance with the foregoing description upon a carrier medium. Suitable carrier media include memory media or storage media such as magnetic or optical media, e.g., disk or CD-ROM, as well as signals such as electrical, electromagnetic, or digital signals, conveyed via a communication medium such as networks and/or a wireless link.

The software for the system may be used to measure and determine the metal contamination of additional semiconductor topographies. In some embodiments, a predefined algorithm for the metal contamination may be incorporated into the software package that interfaces with a system which may be configured to measure the metal contamination in a semiconductor topography. In this manner, the software may be configured to receive electrical property data that may be measured by a sensor incorporated into the system. The software may also be configured to perform appropriate calculations to convert the electrical property data into a characteristic of the metal contamination in the semiconductor topography. Additionally, the software may also be configured to compare an electrical property of a product semiconductor topography to an electrical property of a reference semiconductor topography having a predetermined amount of a known type of metal contamination. Furthermore, the software may be configured to receive electrical property data that may be measured as a function of a position of the semiconductor topography. In this manner, the software may be configured to generate a plot of the measured electrical properties or determined characteristics of the metal contamination as a function of the measurement position. In addition, the software may be configured to determine variations in the electrical properties as a function of the measurement position and to determine locally contaminated regions of the semiconductor substrate.

Figure 4:
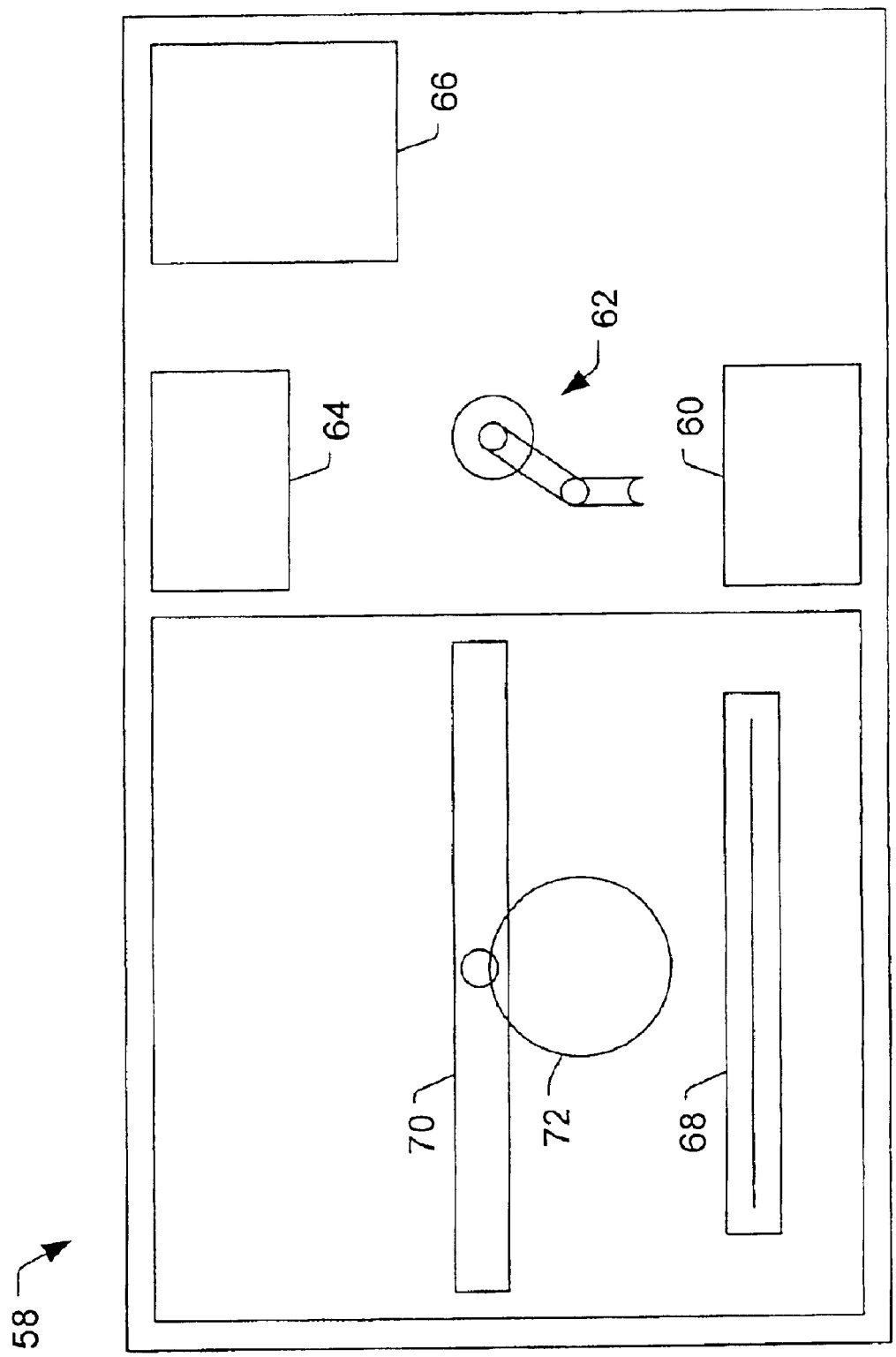
FIG. 4 depicts a plan view of a system configured to measure a characteristic of metal contamination in a semiconductor topography.

FIG. 4 illustrates a plan view of an embodiment of a system that may be configured to measure a characteristic of metal contamination on a semiconductor topography. The semiconductor topography may include a semiconductor substrate or a dielectric material disposed upon a semiconductor substrate. A semiconductor topography may be placed into wafer cassette 60. Wafer cassette 60 may be, loaded into system 58. System 58 may include robotic handler 62 which may be configured to pick up a semiconductor topography and to move the semiconductor topography from one device of the system to another device of the system. System 58 may also include pre-aligner 64 which may be configured to alter a position of the semiconductor topography. For example, pre-aligner 64 may alter a position of each semiconductor topography such the orientation of each semiconductor topography may be substantially the same during processing. Alternatively, the pre-aligner may be configured to detect an alignment mark formed on the semiconductor topography and to alter a position of the semiconductor topography such that a position of the alignment mark may be substantially the same as a predetermined position.

In an embodiment, system 58 may also include oven 66 which may be used to anneal a semiconductor topography. Oven 66 may be configured to heat the semiconductor substrate to a temperature of less than approximately 1100° C. The oven may also be configured to drive the metal contamination into a dielectric material of the semiconductor topography or into a semiconductor substrate of the semiconductor topography. System 58 may also include a cooling device (not shown), which may be used to reduce a temperature of the semiconductor topography subsequent to the annealing process. The cooling device may include any such device known in the art, such as a chill plate.

In an embodiment, system 58 may include device 68 which may be used to deposit a charge on an upper surface of the semiconductor topography. Device 68 may include a non-contact corona charging device such as a needle corona source or a wire corona source. Additional examples of non-contact corona charging devices are illustrated in U.S. Pat. No. 4,599,558 to Castellano et al., U.S. Pat. No. 5,594,247 to Verkuil et al., and U.S. Pat. No. 5,644,223 to Verkuil and are incorporated by reference as if fully set forth herein. The deposited charge may be positive or negative depending on the parameters of the device that may be used to deposit the charge. The device may be used to deposit a charge on predetermined regions of the semiconductor topography and on randomly determined regions of the semiconductor topography. In addition, the device may also be used to deposit a charge on a portion of the semiconductor topography or on substantially the entire semiconductor topography.

In an embodiment, system 58 may also include sensor 70 which may be used to measure at least one electrical property of the charged upper surface of the semiconductor topography. The sensor may be configured to operate as a non-contact work function sensor or a surface photo-voltage sensor. The non-contact work function sensor may include, e.g., a Kelvin probe sensor or a Monroe sensor. Additional examples of work function sensors which may be incorporated into the system are illustrated in U.S. Pat. No. 4,812,756 to Curtis et al., U.S. Pat. No. 5,485,091 to Verkuil, U.S. Pat. No. 5,650,731 to Fung and U.S. Pat. No. 5,767,693 to Verkuil and are incorporated by reference as if fully set forth herein. Sensor 70 may be used to measure electrical properties, which may include, but are not limited to, a tunneling voltage, a surface voltage, and a surface voltage as a function of time. System 58 may also include an illumination system (not shown) which may be configured to direct a pulse of light toward the semiconductor topography and which may be used to generate a surface photo-voltage of the semiconductor substrate. As such, an electrical property that may be measured by sensor 70 may also include a surface photo-voltage of the semiconductor substrate. System 58 may further include movable chuck 72 which may be used to alter a position of the semiconductor topography under device 68, under an illumination system, and under sensor 70. As such, system 58 may be used to measure an electrical property of the semiconductor topography as a function of time and position of the semiconductor topography.

In an additional embodiment, system 58 may also include an operating system (not shown) which may be used to monitor and control the operation of oven 66 to heat the semiconductor substrate to an anneal temperature. The operating system may also be configured to monitor and control the operation of device 68 to deposit a charge on an upper surface of the semiconductor topography. Additionally, the operating system may be further configured to monitor and control the operation of sensor 70 to measure an electrical property of the semiconductor topography. Furthermore, the operating system may be used to determine a characteristic of the metal contamination in the semiconductor topography. The characteristic of the metal contamination in the semiconductor topography may be determined as a function of the measured electrical property. In addition, the operating system may also be configured to monitor and control an additional device of the operating system including a robotic wafer handler, a pre-aligner, a wafer chuck, and/or an illumination system.

Figure 5:
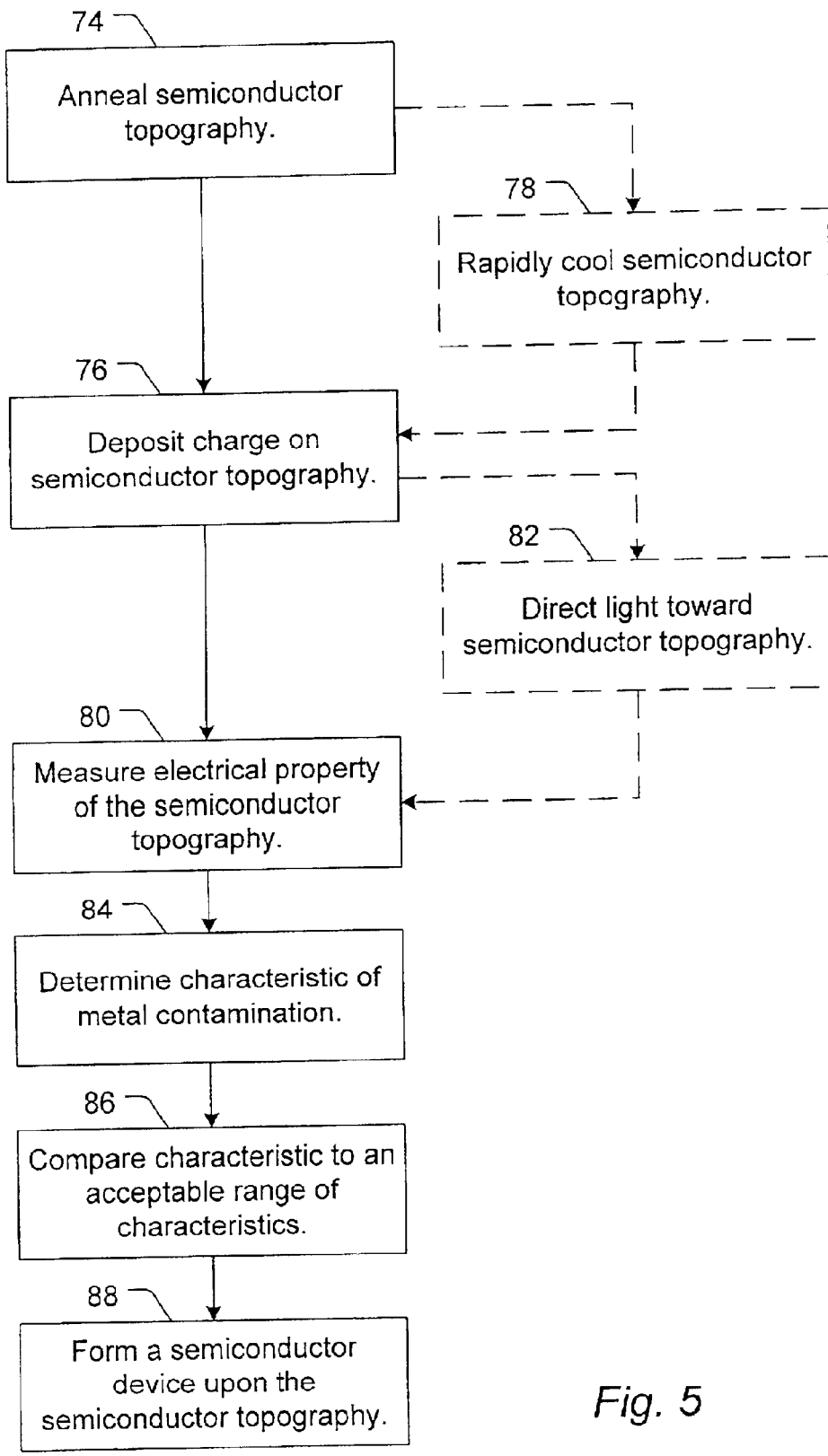
FIG. 5 depicts a flow chart illustrating a method to fabricate a semiconductor device that may include forming the semiconductor device on a semiconductor topography if a characteristic of the metal contamination is within a range of acceptable characteristics of the metal contamination.

FIG. 5 illustrates an embodiment of a method for fabricating a semiconductor device. The method may include annealing a semiconductor topography as shown in step 74. The annealed semiconductor topography may be substantially free of damage. The semiconductor topography may include a semiconductor substrate or a dielectric material formed upon a semiconductor substrate. Appropriate semiconductor substrates may include monocrystalline silicon, silicon germanium, and gallium arsenide. The dielectric material may include, but may not be limited to, silicon dioxide, silicon nitride, silicon oxynitride, and various low-k and high-k materials. The method may be used to determine various types of metal contamination including, but not limited to, copper, iron, chromium, cobalt, and aluminum.

The annealing process of step 74 may include heating the semiconductor topography to an annealing temperature such that only one type of metal contamination may be driven into the semiconductor topography. Alternatively, the annealing process may be performed to drive at least two types of metal contamination into the semiconductor topography. For example, the annealing process may include heating the semiconductor topography to a temperature of less than 1100° C. The semiconductor topography may be heated to a temperature that may depend on the metal contamination which may be driven into the semiconductor topography. For copper metal contamination, the annealing process may include heating the semiconductor topography to a temperature of approximately 350° C. to approximately 500° C. The annealing process may also include heating the semiconductor topography for a period of time. The period of time may be longer or shorter depending on the type of metal contamination that may be driven into the semiconductor topography. For example, for copper metal contamination, the annealing process may include heating the semiconductor topography for approximately one minute to approximately thirty minutes. The annealing process may be used to drive the metal contamination into the semiconductor substrate of the semiconductor topography or into the dielectric material of the semiconductor topography. As shown in step 78, the semiconductor topography may be rapidly cooled subsequent to the annealing process. As such, cooling the semiconductor topography may be effective to prevent diffusion of the metal contamination out of the semiconductor substrate.

As shown in step 76, the method may include depositing a charge on an upper surface of the semiconductor topography. As such, the charge may be deposited on an upper surface of a dielectric material or a semiconductor substrate of the semiconductor topography. The charge may be deposited by using a non-contact corona charging technique. The charge may be deposited on predetermined regions of the semiconductor topography or on randomly determined regions of the semiconductor topography. In addition, the charge may be deposited on a portion of the semiconductor topography or on substantially the entire semiconductor topography.

The method may also include measuring at least one electrical property of the semiconductor topography as shown in step 80. Measuring the electrical property may include using a non-contact work function sensor. The electrical property of the semiconductor topography may include, but is not limited to, a tunneling voltage, a surface voltage, and a surface voltage as a function of time. In an embodiment, the method may include directing a pulse of light toward the semiconductor topography prior to measuring the electrical property as shown in step 82. As such, the electrical property of the semiconductor topography may also include a surface photo-voltage of the semiconductor topography.

As shown in step 84, the method may also include determining a characteristic of the metal contamination in the semiconductor topography. The characteristic may be a function of the measured electrical property of the semiconductor topography. The characteristic may also be a function of the temperature to which the semiconductor topography is heated during the annealing process and a function of the amount of charge that may be deposited upon an upper surface of the semiconductor topography. In addition, determining the characteristic may include determining the characteristic of only one types of metal contamination or determining the characteristic of at least two types of metal contamination. Determining the characteristic may also include determining a characteristic of a portion of the semiconductor topography. As such, locally contaminated regions of the semiconductor substrate may be determined.

The method may also include comparing the determined characteristic of the semiconductor topography to a range of acceptable characteristics of the metal contamination as shown in step 86. The range of acceptable characteristics of the metal contamination in the semiconductor topography may include levels of the metal contamination that may not substantially hinder the performance of a semiconductor device, which may be formed thereon. As such, if the characteristic of the metal contamination is within the range of acceptable characteristics as shown in step 88, the method may also include forming a semiconductor device on the semiconductor topography. Alternatively, if the determined characteristic is outside of the acceptable range of characteristics, the semiconductor topography may be further processed to remove the excess metal contamination. Therefore, the method may be repeated for the semiconductor topography subsequent to removal of the excess metal contamination.

A method to measure the metal contamination in a semiconductor topography that includes annealing the semiconductor topography to drive the metal contamination into the semiconductor topography may provide several advantages over current methods that may be used to determine the amount of metal contamination on a semiconductor topography. For example, measuring the metal contamination in the semiconductor topography by annealing the semiconductor topography may provide similar or increased sensitivity in the measurements of the metal contamination. The annealing process may be used to individually determine a characteristic of different types of metal contamination in the semiconductor topography. In addition, the annealing process may be used in conjunction with a second annealing process that may be performed subsequent to depositing a charge on an upper surface of the semiconductor topography. As such, levels of metal contamination that may be measured using the method may be lower than the level of metal contamination that may be measured with current methods. Furthermore, the method may reduce error in measurements of the metal contamination on a semiconductor topography. For example, because a system which may be configured to carry out the method may be fully controlled by a controller computer, the incidence of operator or random error may be reduced using this method.

A method to measure the metal contamination on a semiconductor topography that may include an annealing process to drive the metal contamination into the semiconductor topography may also provide higher throughput than current methods that may be used to measure the metal contamination. The steps that may be performed to carry out the method may be significantly quicker than a processing sequence, which may be used, in currently available methods. In addition, the data analysis which may be involved in a method that may include an annealing process may be performed significantly faster than the data analysis involved in currently available methods. Furthermore, because the method may be performed without having to form semiconductor devices on the semiconductor topography, the method may b relatively quicker and less costly than currently available methods that may be used to measure the metal contamination. Currently available testing methods may also involve destructive testing techniques, which may include removing a portion of the semiconductor topography during testing. The methods described in the above embodiments, however, may not include destroying a semiconductor topography during the method. Therefore, the methods described in the above embodiments may also reduce the cost associated with measuring the metal contamination in a semiconductor topography. Accordingly, the methods described in the above embodiments provide the advantages of high throughput, low cost, and relatively good sensitivity.

EXAMPLE

Effect of an Annealing Process on Detection of Metal Contamination

Figure 6:
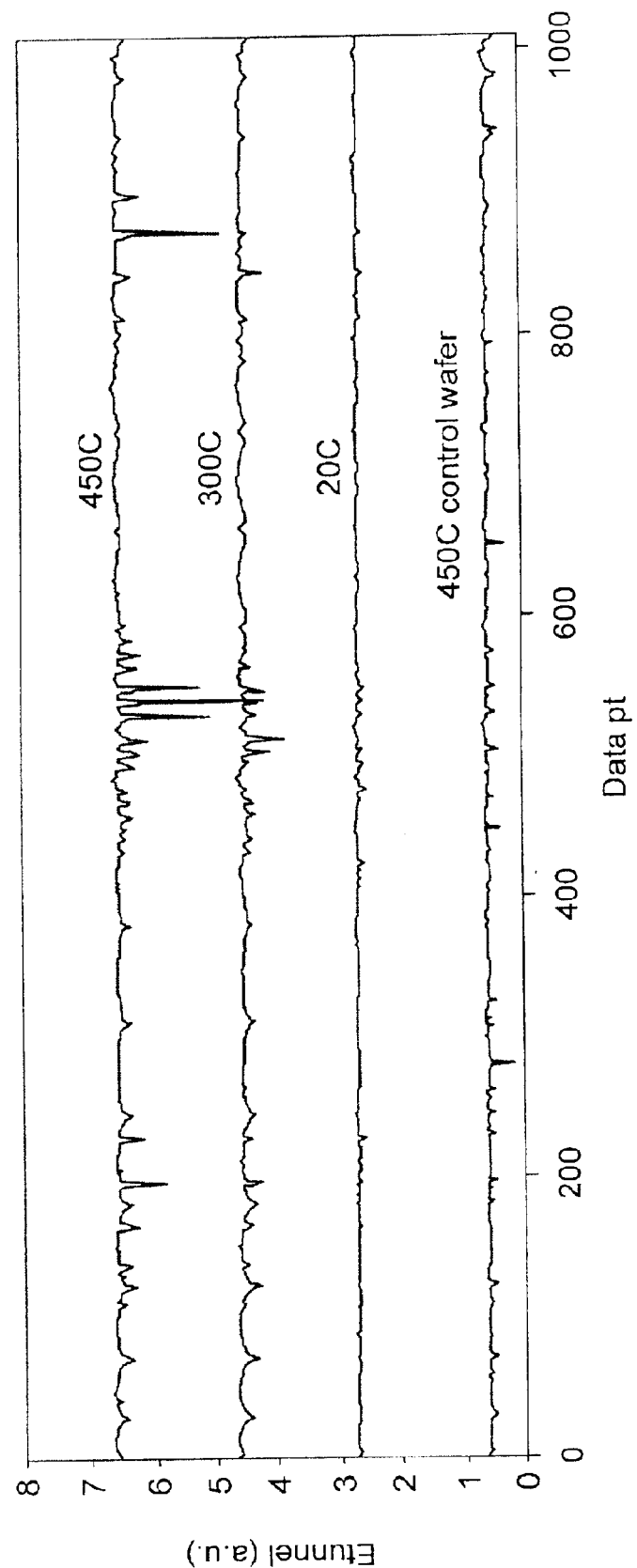
FIG. 6 depicts a plot of the tunneling field of the dielectric material versus annealing temperature.

A silicon dioxide dielectric material was formed on a silicon substrate. An annealing process was performed at various temperatures to drive copper metal contamination into the dielectric material. The temperatures included 20° C., 300° C., and 450° C. A control wafer was also measured after an annealing process, which included heating the semiconductor substrate at 450° C. The control wafer was a silicon dioxide dielectric material formed on a silicon semiconductor substrate which was substantially free of copper metal contamination. A charge was deposited on an upper surface of each dielectric material. The tunneling voltage of the dielectric material was measured at various positions on the semiconductor substrate. In addition, the tunneling, field was determined as a function of the tunneling voltage at each measurement position. FIG. 6 illustrates a plot of the tunneling field at each measurement position on the semiconductor substrate as a function of the various annealing temperatures. Degradation of the silicon dioxide is a function of the temperature of the annealing process. As shown in FIG. 6, copper contamination significantly degrades the tunneling field at annealing temperatures above approximately 300° C.

Figure 7:
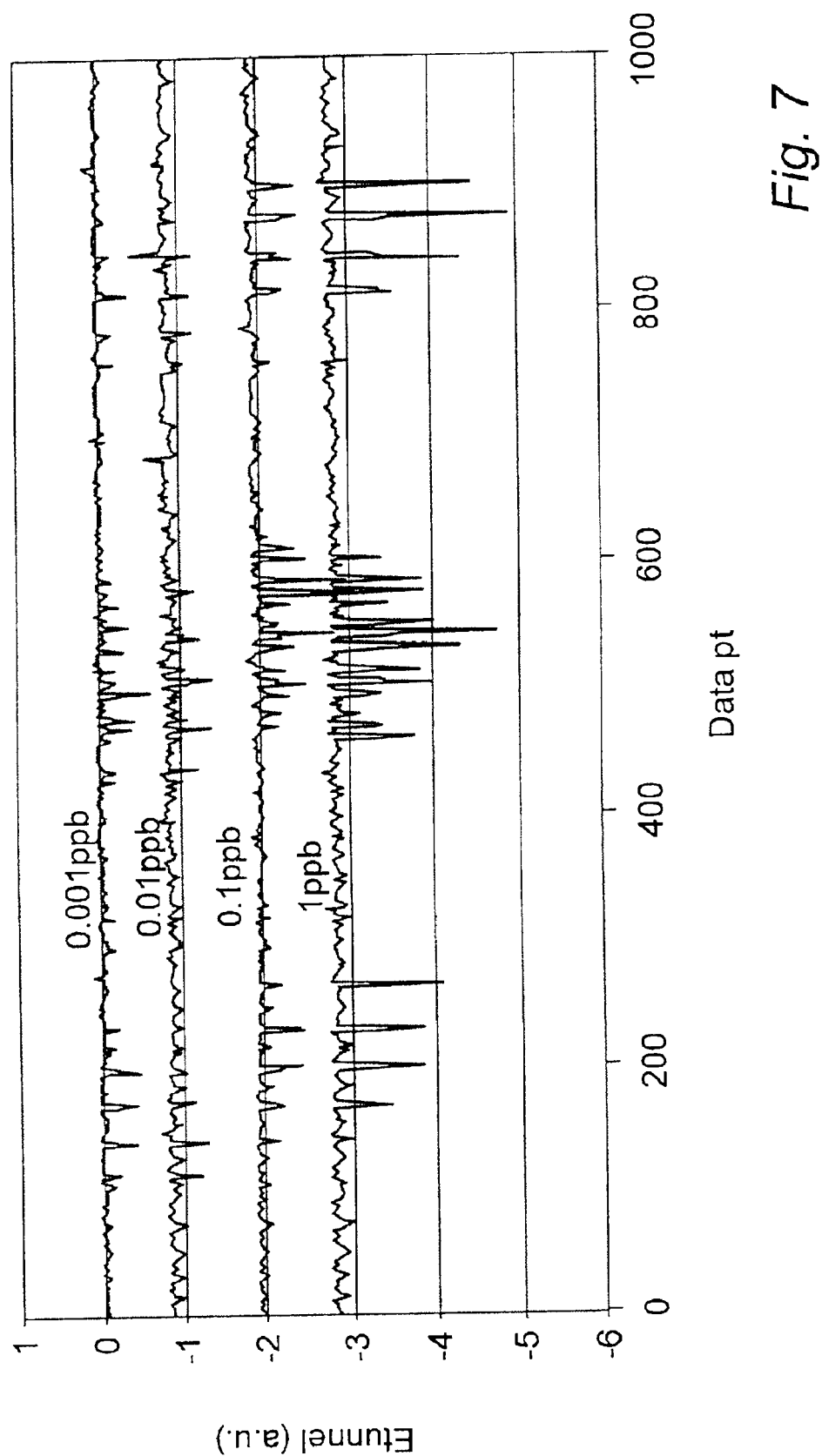
FIG. 7 depicts a plot of the tunneling field of a dielectric material versus levels of metal contamination in the dielectric material.

Several semiconductor substrates were also intentionally contaminated with various levels of copper metal contamination. The copper metal contamination was intentionally deposited on the upper surface of the semiconductor substrates at levels including 1 part per billion (ppb), 0.1 ppb, 0.01 ppb, and 0.001 ppb. The semiconductor substrates were silicon with a silicon dioxide dielectric material layer formed on an upper surface of the silicon. An annealing process was performed to heat each of the semiconductor substrates to an annealing temperature. A charge was deposited on each semiconductor substrate, and a tunneling voltage of the dielectric material was measured at various positions on the semiconductor substrate. A tunneling field was determined at each measurement position on the semiconductor substrate. The tunneling field was plotted versus the measurement position on the semiconductor substrate as shown in FIG. 7. As shown in FIG. 7, the tunneling field is sensitive to a concentration level of 0.001 ppb of copper.

Figure 8:
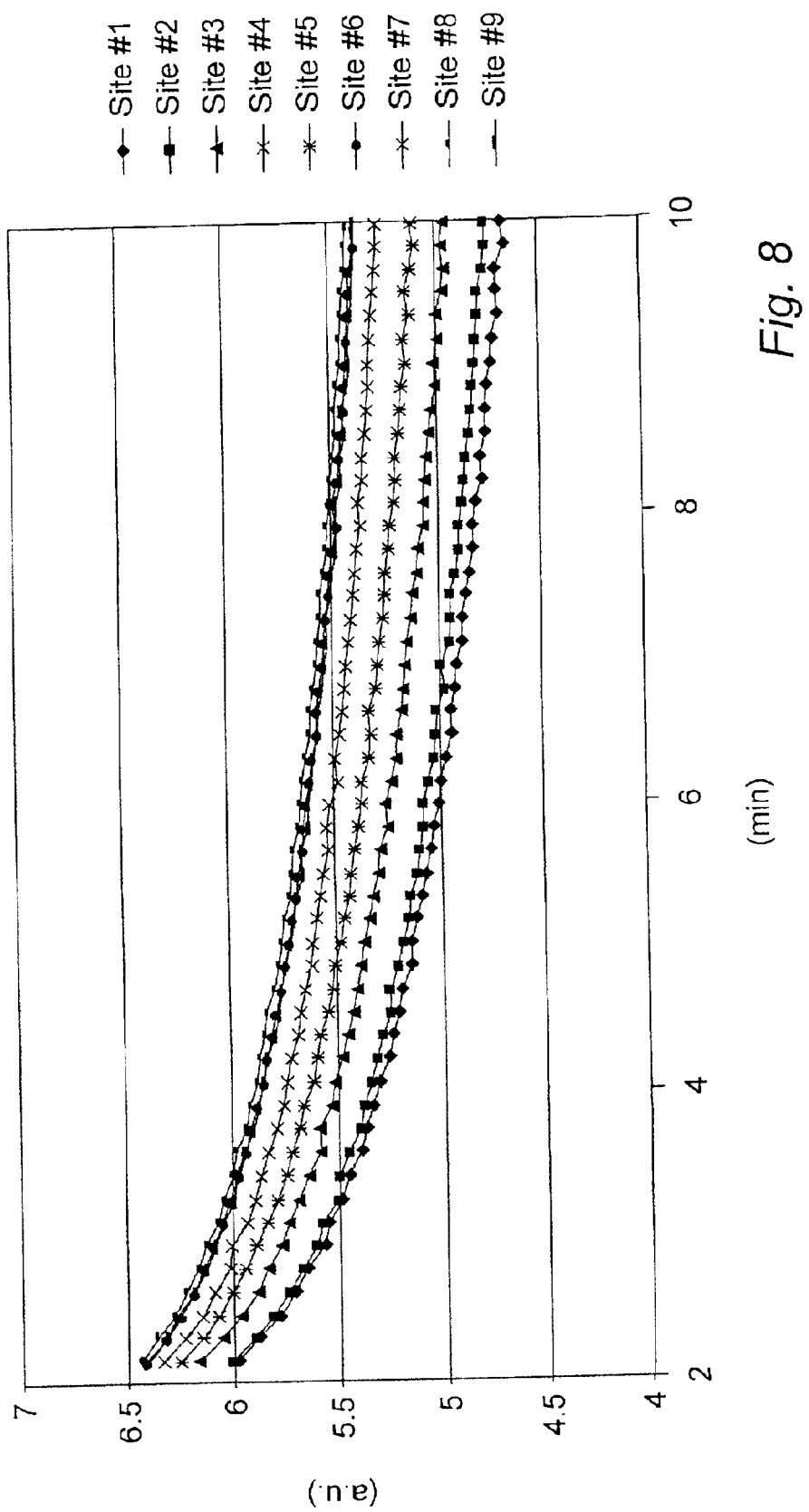
FIG. 8 depicts a plot of the tunneling field of a dielectric material versus the period of time between depositing a charge on an upper surface of the dielectric material and measuring the tunneling voltage of the dielectric material.

A silicon semiconductor substrate having a silicon dioxide dielectric material was intentionally contaminated with copper at various positions on the semiconductor substrate. An annealing process was performed to heat the semiconductor substrate to an annealing temperature to drive the copper contamination into the silicon dioxide. A charge was deposited on an upper surface of the silicon dioxide, and a tunneling voltage was measured as a function of time at each of the positions on the semiconductor substrate. A tunneling field was determined using the tunneling voltage as a function of time at each of the positions on the semiconductor substrate. A relative tunneling field was plotted versus the time between depositing the charge and measuring the tunneling voltage for each measurement position as shown in FIG. 8. The positions at which the semiconductor substrate were contaminated with copper include Site #1 to Site #6. Sites #7 to #9 of the semiconductor substrate were intentionally prevented from being contaminated with copper metal contamination. As shown in the plotted data of FIG. 8, for copper contamination, a delay time of approximately two minutes to approximately ten minutes between depositing the charge on the upper surface of the dielectric material and measuring the tunneling voltage of the dielectric material may be effective to obtain an optimized sensitivity in the measurements of the tunneling field.

Figure 9:
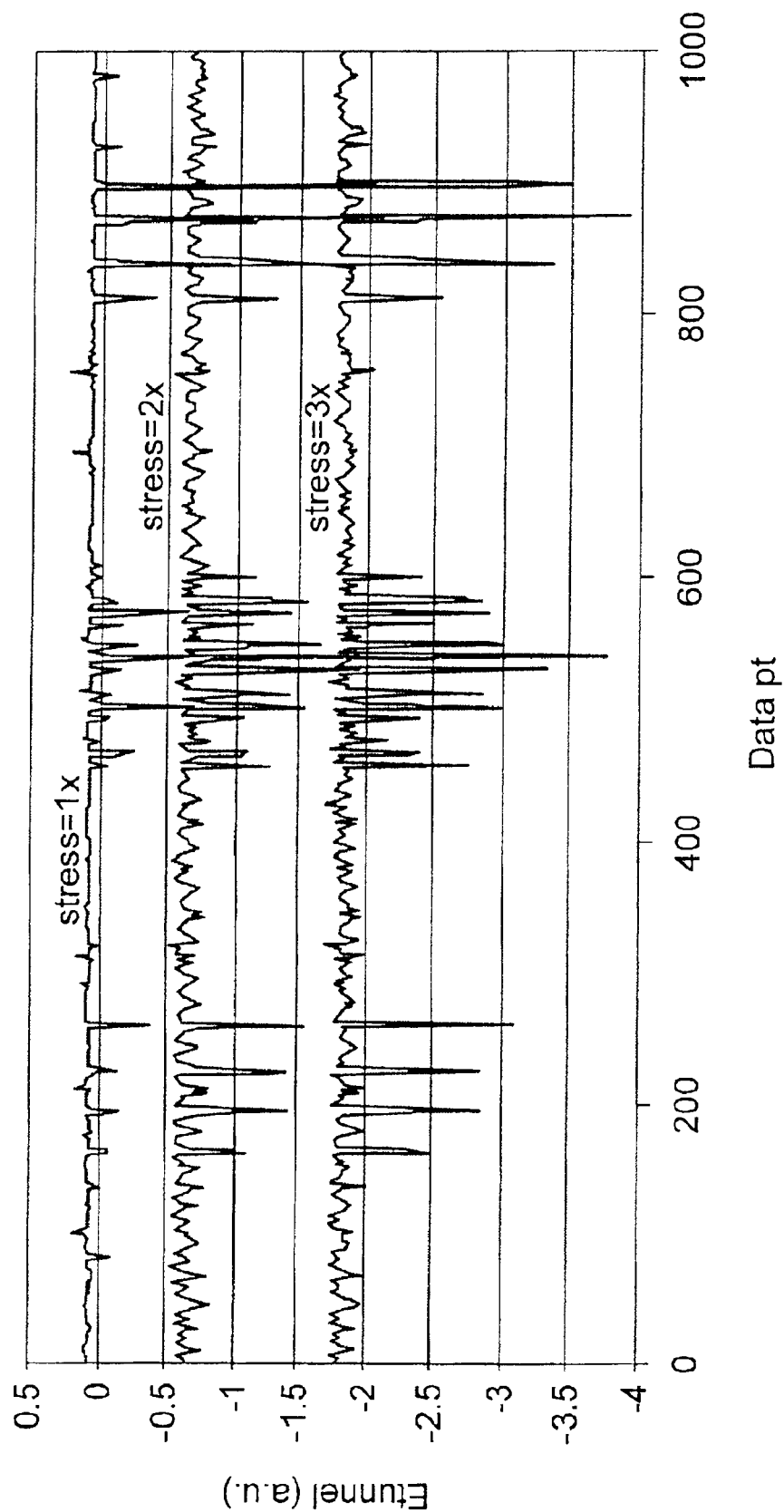
FIG. 9 depicts a plot of the tunneling field of a dielectric material versus the number of electrical stress cycles performed on the dielectric material.

A silicon semiconductor substrate having a silicon dioxide dielectric, material was intentionally contaminated with copper at various positions on the semiconductor substrate. An annealing process was performed to heat the semiconductor substrate to an annealing temperature to drive the copper contamination into the silicon dioxide. A charge was deposited on an upper surface of the silicon dioxide, and the semiconductor substrate was subjected to a number of electrical stress cycles. The electrical stress cycle was performed by depositing a charge on the upper surface of the semiconductor substrate and heating the semiconductor substrate subsequent to depositing the charge. A tunneling voltage was measured as a function of the measurement position on the semiconductor substrate after each of three electrical stress cycles. A tunneling field was determined using the tunneling voltage at each measurement position on the semiconductor substrate and after each of three electrical stress cycles. The tunneling field at each measurement position after each electrical stress cycle was plotted for the dielectric material is shown in FIG. 9. FIG. 9 illustrates that the detection capability of the method of an above embodiment increases after each electrical stress cycle.

Figure 10:
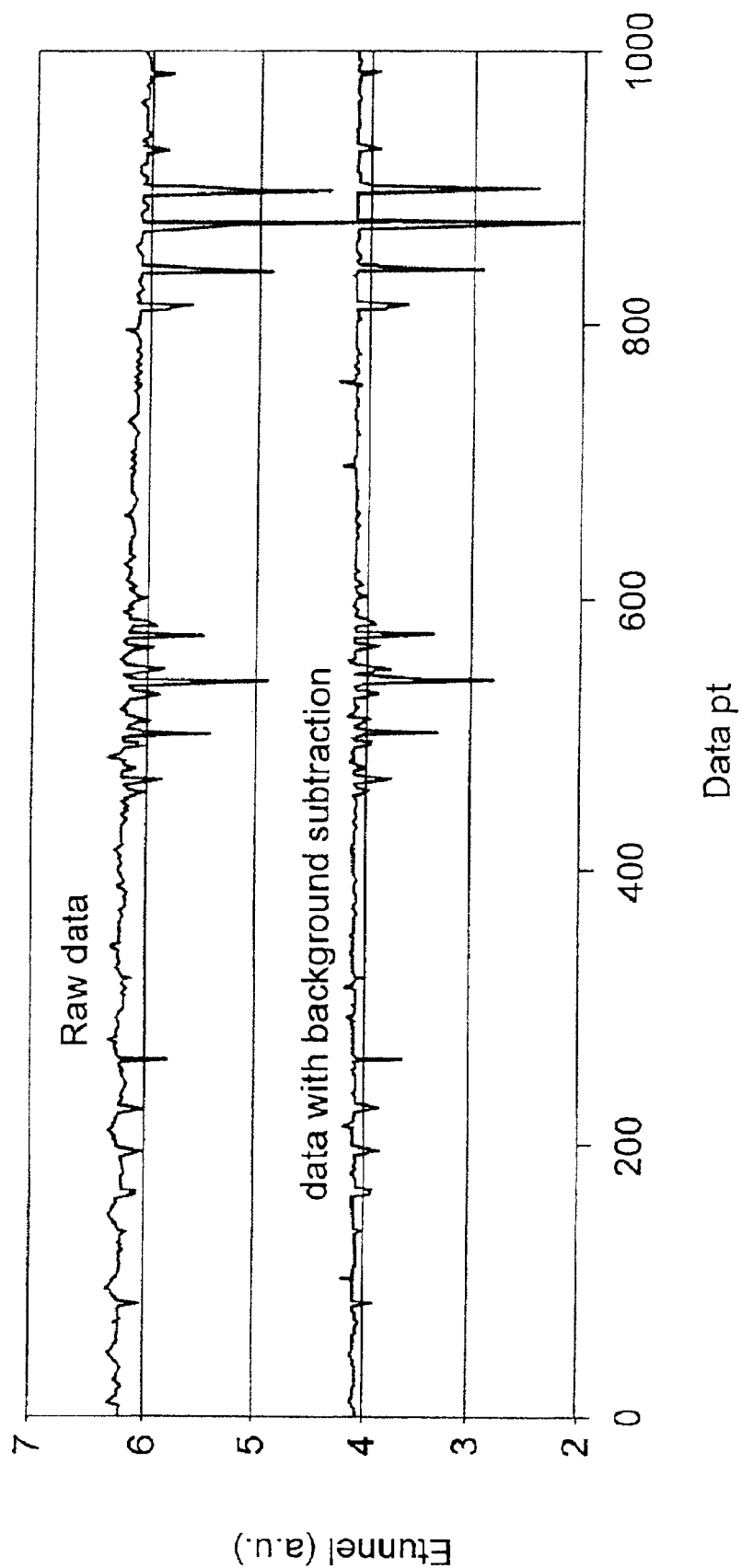
FIG. 10 depicts a plot of tunneling field data versus measurement position on the dielectric material that illustrates the differences between measured data before and after background subtraction.
Figure 11:
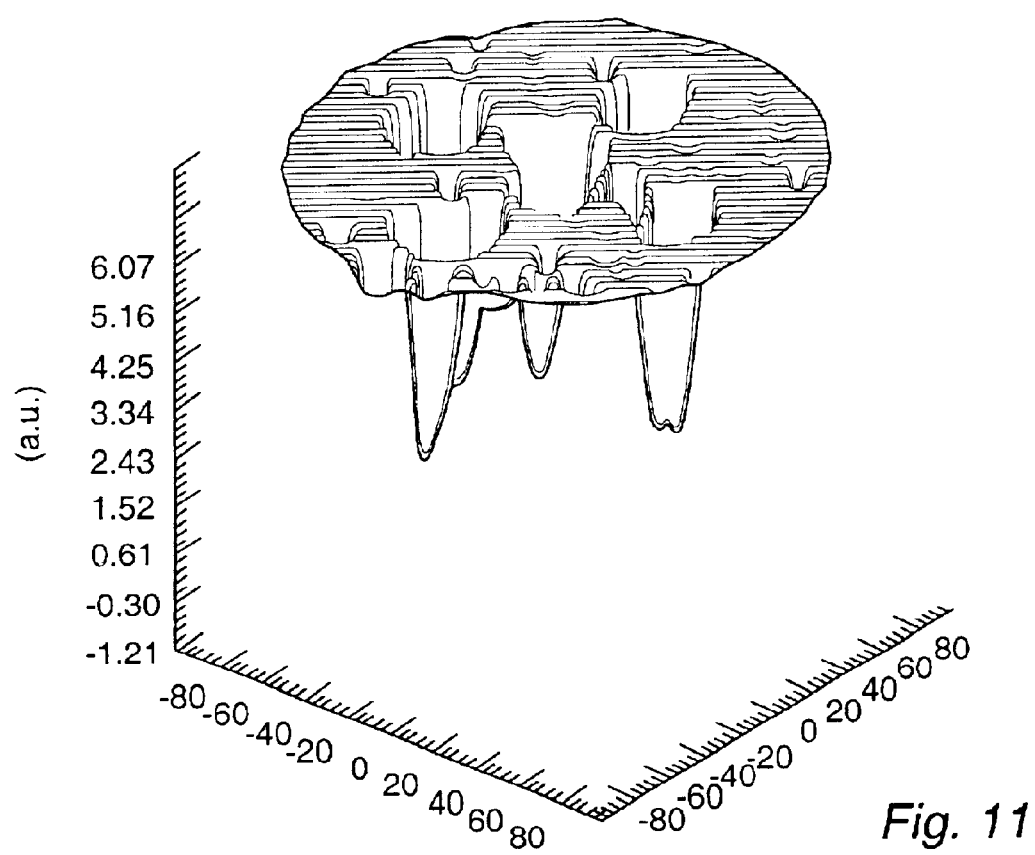
FIG. 11 depicts a plot of the tunneling field of a dielectric material which was intentionally contaminated with copper at five positions on the semiconductor substrate versus the position on the semiconductor substrate at which the measurement was taken.

A silicon semiconductor substrate having a silicon dioxide dielectric material was again intentionally contaminated with copper at various positions on the semiconductor substrate. An annealing process was performed to heat the semiconductor substrate to an annealing temperature to drive the copper contamination into the silicon dioxide. A charge was deposited on an upper surface of the silicon dioxide, and a tunneling voltage was measured as a function of the measurement position on the semiconductor substrate. A tunneling field was determined using the tunneling voltage at each measurement position on the semiconductor substrate. A reference tunneling field of a reference dielectric material was then subtracted from the determined tunneling field of the dielectric material, which is a function of the measured tunneling voltage at each measurement position on the semiconductor substrate. The reference dielectric material was substantially free of the metal contamination. The tunneling field at each measurement position as determined from the measured tunneling voltage and after subtraction of the reference tunneling field is shown in FIG. 10. As shown in FIG. 10, a baseline of the determined tunneling field data may be altered by subtracting the reference tunneling field. FIG. 11 also shows the determined tunneling field data using a whole wafer mapping technique. The technique was used to determine the position of the locally contaminated portions of the dielectric material.

Figure 12:
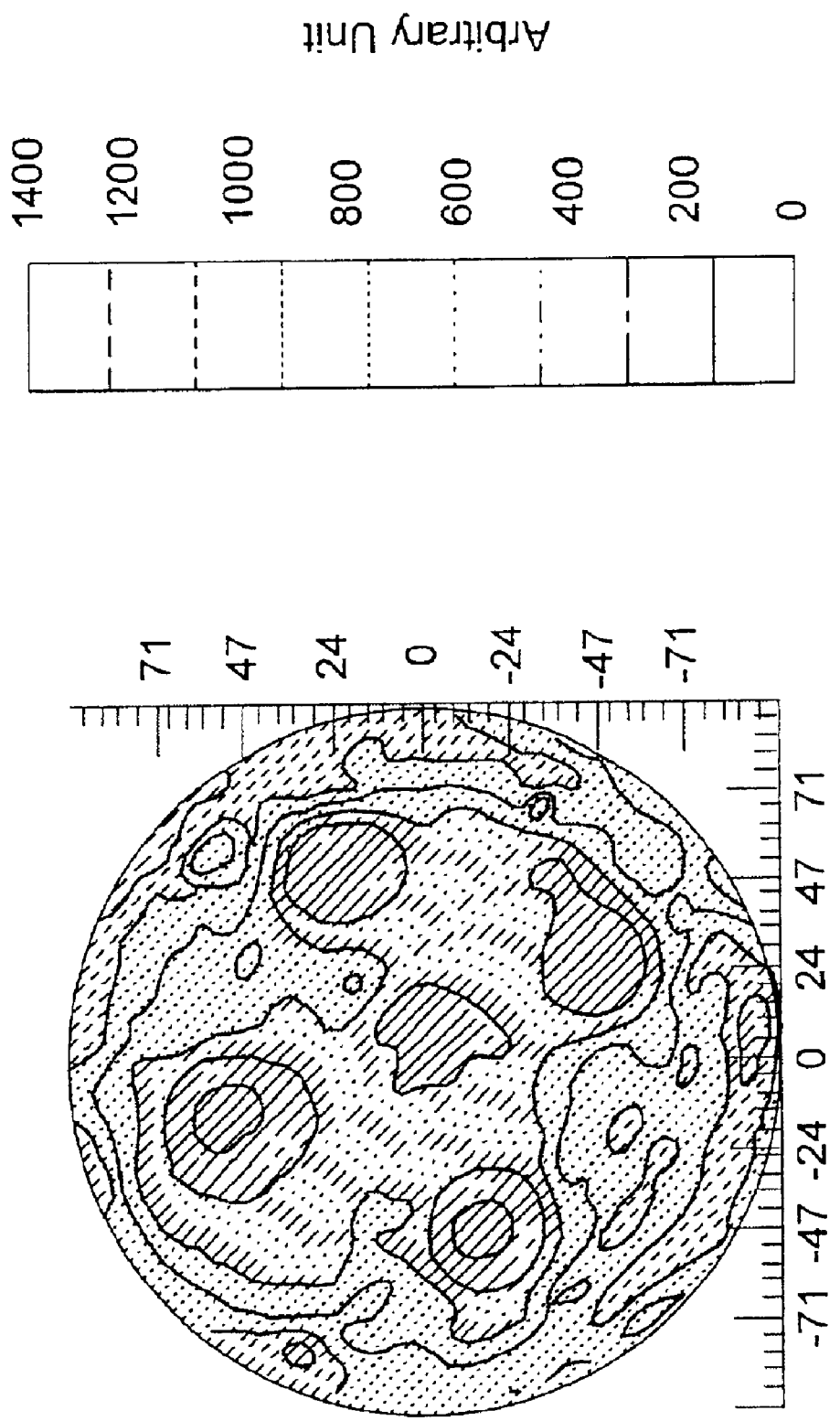
FIG. 12 depicts a plot of bulk minority carrier lifetime of a semiconductor substrate, which was intentionally contaminated with copper at five positions on the semiconductor substrate versus the position on the semiconductor substrate at which the measurement was taken.

An additional silicon semiconductor substrate having a silicon dioxide dielectric material was intentionally contaminated with copper at various positions on the semiconductor substrate. An annealing process was performed to heat the semiconductor substrate to an annealing temperature to drive the copper contamination into the silicon substrate. The semiconductor substrate was rapidly cooled subsequent to the annealing process. A charge was deposited on an upper surface of the silicon dioxide, and a pulse of light was directed toward the semiconductor substrate. A surface photo-voltage was measured as a function of delay time and as a function of the measurement position on the semiconductor substrate. A bulk minority carrier lifetime was determined using the surface photo-voltage at each measurement position on the semiconductor substrate. The bulk minority carrier lifetime at each measurement position as determined from the measured surface photo-voltage is shown in FIG. 12 using a whole wafer mapping technique. The technique was used to determine the position of the locally contaminated portions of the dielectric material using the determined bulk minority carrier lifetime data.

It will be appreciated to those skilled in the art having the benefit of this disclosure that this invention is believed to provide a method to measure the metal contamination in a semiconductor topography which may include annealing the semiconductor topography to drive the metal contamination into a dielectric material or into a semiconductor substrate. Further modifications and alternative embodiments of various aspects of the invention will be apparent to those skilled in the art in view of this description. It is intended that the following claims be interpreted to embrace all such modifications and changes and, accordingly, the specification and drawings are to be regarded in an illustrative rather than a restrictive sense.

What is claimed is:

1. A method for detecting metal contamination in a dielectric material disposed upon a semiconductor substrate, comprising:

annealing the semiconductor substrate, wherein annealing the semiconductor substrate is effective to drive the metal contamination into the dielectric material;

subsequent to said annealing, measuring a tunneling voltage of the dielectric material; and determining a characteristic of the metal contamination in the dielectric material as a function of the measured tunneling voltage.

2. The method of claim 1, wherein the annealed dielectric material is substantially free of damage.

3. The method of claim 1, wherein annealing the semiconductor substrate comprise heating the semiconductor substrate to an annealing temperature, and wherein the metal contamination comprises one type of metal contamination.

4. The method of claim 1, wherein the metal contamination comprises at least two types of metal contamination.

5. The method of claim 1, wherein annealing the semiconductor substrate comprises heating the semiconductor substrate to an annealing temperature of less than approximately 1100° C.

6. The method of claim 1, wherein the metal contamination comprises copper, and wherein annealing the semiconductor substrate comprises heating the semiconductor substrate to an annealing temperature of approximately 350° C. to approximately 500° C.

7. The method of claim 1, wherein the metal contamination comprises copper, wherein annealing the semiconductor substrate comprises heating the semiconductor substrate for a period of time, and wherein the period of time comprises approximately one minute to approximately thirty minutes.

8. The method of claim 1, wherein measuring the tunneling voltage comprises depositing a charge on an upper surface of the dielectric material, and wherein depositing the charge comprises using a non-contact corona charging technique.

9. The method of claim 1, wherein measuring the tunneling voltage comprises depositing a charge on an upper surface of the dielectric material, and wherein the deposited charge comprises approximately $1\times10^{-6}$ $C/cm^2$ to approximately $1\times10^{-4}$ $C/cm^2$ for positive tunneling voltage.

10. The method of claim 1, wherein measuring the tunneling voltage comprises depositing a charge on an upper surface of the dielectric material, and wherein the deposited charge comprises approximately $-1\times10^{31\ r6}$ $C/cm^2$ to approximately $-1\times10^{-4}$ $C/cm^2$ for negative tunneling voltage.

11. The method of claim 1, wherein measuring the tunneling voltage comprises:

depositing a charge on an upper surface of the dielectric material;

waiting for a predetermined period of time after depositing the charge on the upper surface of the dielectric material; and determining the tunneling voltage.

12. The method of claim 1, wherein measuring the tunneling voltage comprises depositing a charge on an upper surface of the dielectric material, and wherein deposing the charge on the upper surface of the dielectric material comprises depositing the charge on predetermined regions of the upper surface of the dielectric material.

13. The method of claim 1, wherein measuring the tunneling voltage comprises depositing a charge on an upper surface of the dielectric material, and wherein depositing the charge on the upper surface of the dielectric material comprises depositing the charge on a portion of the upper surface or on substantially the entire upper surface.

14. The method of claim 1, wherein measuring the tunneling voltage of the dielectric material comprises using a non-contact work function measurement technique.

15. The method of claim 1, further comprising comparing the tunneling voltage of the dielectric material to a tunneling voltage of a reference dielectric material, wherein the reference dielectric material is substantially free of metal contamination.

16. The method of claim 1, further comprising comparing the tunneling voltage of the dielectric material to a tunneling voltage of a reference dielectric material, wherein the reference dielectric material comprises a predetermined level of at least one type of metal contamination, and wherein at least the one type of metal contamination is predetermined.

17. The method of claim 1, further comprising determining a tunneling field of the dielectric material, wherein the tunneling field is a function of the tunneling voltage, the method further comprising comparing the tunneling field of the dielectric material to a tunneling field of a reference dielectric material, wherein the reference dielectric material is substantially free of contamination.

18. The method of claim 1, further comprising determining annealing field of the dielectric material, wherein the tunneling field is a function of the tunneling voltage, the method further comprising comparing the tunneling field of the dielectric material to a tunneling field of a reference dielectric material, wherein the reference dielectric material comprises a predetermined level of at least one type of metal contamination, and wherein at least the one type of metal contamination is predetermined.

19. The method of claim 1, wherein determining the characteristic of the metal contamination in the dielectric material comprises comparing the tunneling voltage of the dielectric material to a tunneling voltage of a reference dielectric material.

20. The method of claim 1, further comprising determining a tunneling field of the dielectric material, wherein the tunneling field is a function of the tunneling voltage.

21. The method of claim 1, further comprising determining a tunneling field of the dielectric material, wherein determining the tunneling field comprises subtracting a tunneling voltage of a reference dielectric material from the tunneling voltage of the dielectric material.

22. The method of claim 1, wherein the characteristic of the metal contamination further comprises a function of a temperature of the annealing of the semiconductor substrate.

23. The method of claim 1, wherein the characteristic of the metal contamination further comprises a function of an amount of a deposited charge.

24. The method of claim 1, wherein determining the characteristic of the metal contamination in the dielectric material comprises determining a characteristic of at least two types of metal contamination in the dielectric material.

25. The method of claim 1, wherein determining the characteristic of the metal contamination in the dielectric material comprises determining a characteristic of at least one type of metal contamination in a portion of the dielectric material, and wherein the portion of the dielectric material comprises a locally contaminated region of dielectric material.

26. The method of claim 1, further comprising measuring the tunneling voltage of the dielectric material at more than one position on the semiconductor substrate, determining a tunneling field of the dielectric material at each position, and determining the characteristic of at least one type of metal contamination at each position.

27. The method of claim 26, further comprising generating a plot of the determined tunneling field as a function of position.

28. The method of claim 27, further comprising comparing the generated plot of the determined tunneling field as a function of position to a plot of a predetermined tunneling field as a function of position.

29. The method of claim 28, wherein the predetermined tunneling field is representative of a range of acceptable levels of at least the one type of metal contamination, and wherein the acceptable levels do not substantially hinder performance of a semiconductor device formed on the semiconductor substrate.

30. The method of claim 1, further comprising annealing the semiconductor substrate subsequent to depositing a charge on an upper surface of the semiconductor substrate.

31. The method of claim 30, further comprising heating the semiconductor substate to an annealing temperature of less than approximately 120° C.

32. The method of claim 30, further comprising heating the semiconductor substrate to an annealing temperature of less than approximately 120° C., wherein the metal contamination comprises copper, and wherein the dielectric material comprises silicon dioxide.

33. The method of claim 1, further comprising generating electrical stress in the dielectric material and heating the semiconductor substrate subsequent to generating the electrical stress in the dielectric material.

34. The method of claim 33, wherein generating the electrical stress comprises using a non-contact corona charging technique, and wherein the electrical stress comprises approximately $-1 \times 10^{-3}$ C/cm$^2$ to approximately $+1 \times 10^{-3}$ C/cm$^2$.

35. The method of claim 33, wherein heating the semiconductor substrate comprises heating the semiconductor substrate to a temperature of approximately 50° C. to approximately 120° C.

36. The method of claim 33, wherein heating the semiconductor substrate comprises heating the semiconductor substrate for a period of time of approximately one minute to approximately thirty minutes.

37. The method of claim 1, further comprising determining a presence of particulate contamination on the dielectric material, wherein the presence of particulate contamination is a function of the measured tunneling voltage.

38. The method of claim 37, further comprising flowing a gas across an upper surface of the dielectric material as a charge is deposited onto the dielectric material.

39. The method of claim 38, wherein the gas has a moisture content, and wherein the moisture content of the gas is greater than a moisture content of air surrounding the semiconductor substrate.

40. The method of claim 38, wherein the gas comprises ammonia.

41. The method of claim 1, wherein the dielectric material comprises silicon dioxide, silicon nitride, or silicon oxynitride.

42. The method of claim 1, wherein the semiconductor substrate comprises monocrystalline silicon, silicon germanium, or gallium arsenide.

43. The method of claim 1, wherein the metal contamination comprises copper.

44. The method of claim 1, wherein the metal contamination comprises iron, chromium, cobalt, or aluminum.

45. The method of claim 1, further comprising comparing the tunneling voltage to a set of data, wherein the set of data comprises tunneling voltages associated with a characteristic of metal contamination.

46. The method of claim 1, further comprising:
re-annealing the semiconductor substrate subsequent to measuring the tunneling voltage; and
re-measuring the tunneling voltage of the dielectric material.

47. A method for increasing degradation of a dielectric material resulting from metal contamination, comprising:
generating electrical stress in the dielectric material, wherein the dielectric material is disposed upon a semiconductor substrate;
heating the semiconductor substrate subsequent to generating the electrical stress in the dielectric material;
subsequent to said heating, measuring a tunneling voltage of the dielectric material; and
determining a characteristic of the metal contamination in the dielectric material, as a function of the measured tunneling voltage.

48. A method for determining a characteristic of metal contamination in a dielectric material disposed upon a semiconductor substrate, comprising:
annealing the semiconductor substrate prior to depositing a charge on an upper surface of the dielectric material, wherein annealing the semiconductor substrate is effective to drive the metal contamination into the dielectric material;
depositing the charge upon the upper surface of the dielectric material;
annealing the semiconductor substrate subsequent to depositing the charge on the upper surface of the dielectric material;
subsequent to said annealing subsequent to said depositing, measuring a tunneling voltage of the dielectric material; and
determining a characteristic of the metal contamination in the dielectric material as a function of the measured tunneling voltage.

49. A method for detecting metal contamination in a dielectric material disposed upon a semiconductor substrate, comprising:
annealing the semiconductor substrate, wherein annealing the semiconductor substrate is effective to drive the metal contamination into the dielectric material;
measuring an electrical property of the dielectric material;
determining a characteristic of the metal contamination in the dielectric material, wherein the characteristic is a function of the measured electrical property; and
determining a presence of particulate contamination on the dielectric material, wherein the presence of particulate contamination is a function of the measured electrical property.

* * * * *

UNITED STATES PATENT AND TRADEMARK OFFICE
CERTIFICATE OF CORRECTION

PATENT NO. : 6,759,255 B2
DATED : July 6, 2004
INVENTOR(S) : Xu et al.

It is certified that error appears in the above-identified patent and that said Letters Patent is hereby corrected as shown below:

Column 23,
Line 31, after the phrase "conductor substrate," please delete "comprise" and substitute therefor -- comprises --.
Line 63, after the phrase "comprises approximately," please delete "-1x10$^{31\ 16}$ C/cm$^2$" and substitute therefor -- -1x10$^{-6}$ C/cm$^2$ --.

Column 24,
Line 9, after the phrase "and wherein," please delete "deposing" and substitute therefor -- depositing --.
Line 41, please delete "annealing field" and substitute -- a tunneling field --.

Column 25,
Line 33, after the phrase "the semiconductor," please delete "substate"and substitute therefor -- substrate --.

Signed and Sealed this

Seventh Day of December, 2004

JON W. DUDAS
*Director of the United States Patent and Trademark Office*